US010190115B2

(12) United States Patent
Saxonov

(10) Patent No.: US 10,190,115 B2
(45) Date of Patent: *Jan. 29, 2019

(54) METHODS AND COMPOSITIONS FOR NUCLEIC ACID ANALYSIS

(71) Applicant: Bio-Rad Laboratories, Inc., Hercules, CA (US)

(72) Inventor: Serge Saxonov, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 331 days.

This patent is subject to a terminal disclaimer.

(21) Appl. No.: 14/493,272

(22) Filed: Sep. 22, 2014

(65) Prior Publication Data

US 2015/0011430 A1  Jan. 8, 2015

Related U.S. Application Data

(63) Continuation of application No. 13/456,121, filed on Apr. 25, 2012, now Pat. No. 9,347,059.

(60) Provisional application No. 61/478,777, filed on Apr. 25, 2011.

(51) Int. Cl.
| | | |
|---|---|---|
| *C12N 15/00* | (2006.01) | |
| *C12Q 1/68* | (2018.01) | |
| *C12N 15/10* | (2006.01) | |
| *C12Q 1/6876* | (2018.01) | |

(52) U.S. Cl.
CPC ......... *C12N 15/1065* (2013.01); *C12N 15/10* (2013.01); *C12N 15/1075* (2013.01); *C12Q 1/6876* (2013.01)

(58) Field of Classification Search
None
See application file for complete search history.

(56) References Cited

U.S. PATENT DOCUMENTS

| | | |
|---|---|---|
| 3,575,220 A | 4/1971 | Davis et al. |
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 4,988,617 A | 1/1991 | Landegren et al. |
| 5,055,390 A | 10/1991 | Weaver et al. |
| 5,176,203 A | 1/1993 | Larzul |
| 5,225,332 A | 7/1993 | Weaver et al. |
| 5,242,794 A | 9/1993 | Whiteley et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,494,810 A | 2/1996 | Barany et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,789,206 A | 8/1998 | Tavtigian et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,180,349 B1 | 1/2001 | Ginzinger et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,372,813 B1 | 4/2002 | Johnson et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |

(Continued)

FOREIGN PATENT DOCUMENTS

| | | |
|---|---|---|
| EP | 1522582 A2 | 4/2005 |
| EP | 1522582 B1 | 4/2007 |

(Continued)

OTHER PUBLICATIONS

Epicentre Forum Newsletter, 2009, vol. 16-3, p. 4-6.

(Continued)

*Primary Examiner* — James Martinell
(74) *Attorney, Agent, or Firm* — Kilpatrick Townsend and Stockton LLP

(57) ABSTRACT

Provided herein are methods, compositions, and kits for assays, many of which involve amplification reactions such as digital PCR or droplet digital PCR. The assays may be used for such applications as sequencing, copy number variation analysis, and others. In some cases, the assays involve subdividing a sample into multiple partitions (e.g., droplets) and merging the partitions with other partitions that comprise adaptors with barcodes.

26 Claims, 3 Drawing Sheets

(56) References Cited

U.S. PATENT DOCUMENTS

| | | |
|---|---|---|
| 6,558,916 B2 | 5/2003 | Veerapandian et al. |
| 6,575,188 B2 | 6/2003 | Parunak |
| 6,582,938 B1 | 6/2003 | Su et al. |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,074,600 B2 | 7/2006 | Dean et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,537,897 B2 | 5/2009 | Brenner et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,080,380 B2 | 12/2011 | Chee et al. |
| 8,304,193 B2 | 11/2012 | Ismagilov et al. |
| 8,329,407 B2 | 12/2012 | Ismagilov et al. |
| 8,399,198 B2 | 3/2013 | Hiddessen et al. |
| 8,822,148 B2 | 9/2014 | Ismagilov et al. |
| 8,889,083 B2 | 11/2014 | Ismagilov et al. |
| 9,347,059 B2 * | 5/2016 | Saxonov ............ C12N 15/10 |
| 9,644,204 B2 * | 5/2017 | Hindson .......... C12N 15/1065 |
| 9,689,024 B2 | 6/2017 | Hindson et al. |
| 9,695,468 B2 | 7/2017 | Hindson et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0077572 A1 | 4/2007 | Tawfik et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |

(56) References Cited

U.S. PATENT DOCUMENTS

| | | |
|---|---|---|
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0098555 A1 | 4/2009 | Roth et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022403 A1 | 1/2010 | Kurn et al. |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0130369 A1 | 5/2010 | Shenderov et al. |
| 2010/0137163 A1 | 6/2010 | Link et al. |
| 2010/0173394 A1 | 7/2010 | Colston, Jr. et al. |
| 2010/0203538 A1 | 8/2010 | Dube et al. |
| 2010/0233696 A1 | 9/2010 | Joseph et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0033854 A1 | 2/2011 | Drmanac et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0097716 A1 | 4/2011 | Natt et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0270295 A1* | 10/2012 | Choo ............... A61K 9/501 435/178 |
| 2012/0302448 A1 | 11/2012 | Hutchison et al. |
| 2012/0309002 A1 | 12/2012 | Link |
| 2012/0316074 A1 | 12/2012 | Saxonov |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |
| 2013/0295568 A1 | 11/2013 | Link |
| 2014/0155295 A1 | 6/2014 | Hindson et al. |
| 2014/0227684 A1 | 8/2014 | Hindson et al. |
| 2014/0235506 A1 | 8/2014 | Hindson et al. |
| 2014/0287963 A1 | 9/2014 | Hindson et al. |
| 2015/0005199 A1 | 1/2015 | Hindson et al. |
| 2015/0011432 A1 | 1/2015 | Saxonov |

FOREIGN PATENT DOCUMENTS

| | | |
|---|---|---|
| GB | 1 503 163 | 3/1978 |
| GB | 2 097 692 | 11/1982 |
| JP | 295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/023163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | WO 2004/105734 A1 | 12/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | WO 2005/023331 A2 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2006/096571 A2 | 9/2006 |
| WO | 2007/001448 A2 | 1/2007 |
| WO | 2007/091228 | 8/2007 |
| WO | 2007/091230 | 8/2007 |
| WO | 2007/092473 A2 | 8/2007 |
| WO | 2007/133710 | 11/2007 |
| WO | 2008/021123 | 2/2008 |
| WO | 2008/024114 | 2/2008 |

(56) References Cited

FOREIGN PATENT DOCUMENTS

| | | |
|---|---|---|
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2008/134153 A1 | 11/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2010/036352 A1 | 4/2010 |
| WO | 2011/007138 A1 | 1/2011 |
| WO | 2011/034621 | 3/2011 |
| WO | WO 2011/047870 A1 | 4/2011 |
| WO | 2011/079176 | 6/2011 |
| WO | 2012/024543 A1 | 2/2012 |

OTHER PUBLICATIONS

Caruccio et al., "Nextera TM Technology for NGS DNA Library Preparation: Simultaneous Fragmentation and Tagging by In Vitro Transposition", *Epicentre Forum Newsltter*, vol. 16-3, p. 4-6 (Oct. 2009).

Office Action dated Feb. 26, 2016 for Japanese Patent Application No. 2014-508522, with English translation, 9 pages.

U.S. Appl. No. 13/966,150, filed Aug. 13, 2013 (51 pages).

Gyarmati et al., Reversible Disulphide Formation in Polymer Networks: A Versatile Functional Group From Synthesis to Applications, European Polymer Journal, 2013, 49, 1268-1286.

International search report and written opinion dated Oct. 16, 2012 for PCT/US2012/035030.

3M Specialty Materials, "3M Fluorinert Electronic Liquid FC-3283," product information guide, issued Aug. 2001.

Goldschmidt GMBH, "Abil® EM 90 Emulsifier for the formulation of cosmetic W/0 creams *and* lotions," degussa. creating essentials brochure, pp. 1-7, May 2003.

Labsmith, "CapTite™ Microfluidic Interconnects" webpage, downloaded Jul. 11, 2012.

Labsmith, "Microfluid Components" webpage, downloaded Jul. 11, 2012.

Polydimethylsiloxane, 5 pgs., published in FNP 52 (1992).

SOLID system barcoding, Applied Biosystems. 2008. Available at http://www3.appliedbiosystems.com/cms/groups/mcb_marketing/documents/generaldo cuments/cms_057554.pdf. Accessed Apr. 3, 2012.

Thinxxs Microtechnology AG, "Emerald Biosystems: ProteinCrystallization," 1 pg., downloaded Mar. 8, 2011

Anna et al., "Formation of dispersions using "flow focusing" in microchannels," Applied Physics Letters, vol. 82, No. 3, Jan. 20, 2003.

Abate et al., "Functionalized glass coating for PDMS microfluidic devices," Lab on a Chip Technology: Fabrication and Microfluidics, 11 pgs., (2009).

Abdelgawad et al., "All-terrain droplet actuation," Lab on aChip, vol. 8, pp. 672-677, Apr. 2, 2008.

Alexandridis, P., Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Avilion et al., "Human Telomerase RNA and Telomerase Activity in Immortal Cell Lines and Tumor Tissues," Cancer Research 56, pp. 645-650, Feb. 1, 1996.

Baroud et al., "Thermocapillary valve for droplet production and sorting," Physical Review E 75, 046302, pp. 046302-1-046302-5, Apr. 5, 2007.

Beer et al., "Monodisperse droplet generation and rapid trapping for single molecule detection and reaction kinetics measurement," Lab on a Chip, vol. 9, pp. 841-844, Dec. 5, 2008.

Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.

Beer et al., "On-Chip, Real-Time, Single-Copy Polymerase Chain Reaction in Picoliter Droplets," Analytical Chemistry, vol. 79, No. 22, pp. 8471-8475, Nov. 15, 2007.

Bhat et al., "Effect of sustained elevated temperature prior to amplification on template copy number estimation using digital polymerase chain reaction," Analyst, vol. 136, pp. 724-732, (2011).

Blow, N., "PCR's next frontier," Nature Methods, vol. 4, No. 10, pp. 869-875, Oct. 2007.

Bransky et al., "A microfluidic droplet generator based on a piezoelectric actuator," Lab on a Chip, vol. 9, pp. 516-520,Nov. 20, 2008.

Brouzes, et al., Droplet microfluidic technology for single-cell high-throughput screening. Proc Natl Acad Sci US A. Aug. 25, 2009;106(34):14195-200.

Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.

Cawthon, R.M., "Telomere measurement by quantitative PCR," Nucleic Acids Research, vol. 30, No. 10, pp. 1-6, (2002).

Cawthon, Richard M., "Telomere length measurement by a novel monochrome multiplex quantitative PCR method," Nucleic Acids Research, vol. 37, No. 3, pp. 1-7, (2009).

Chabert et al., "Droplet fusion by alternating current (AC) field electrocoalescence in microchannels," Electrophoresis, vol. 26, pp. 3706-3715, (2005).

Chen et al., "Janus Particles Templated from Double EmulsionDroplets Generated Using Microfluidics," Langmuir, vol. 29, No. 8, pp. 4320-4323, Mar. 18, 2009.

Chen et al., "Using Three-Phase Flow ofImmiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).

Chittofrati et al., "Perfluoropolyether microemulsions," Progress inColloid & Polymer Science 79, pp. 218-225, (1989).

Chloroform (Phenomenex), Solvent Miscibility Table, Internet ArchiveWayBackMachine, 3 pgs., Feb. 1, 2008

Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.

Darocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Dasgupta et al., "Light emitting diode-based detectors Absorbance, fluorescence and spectroelectrochemical measurements in a planar flow-through cell," Analytica Chimica Acta 500, pp. 337-364, (2003).

Diehl et al., "Digital quantification of mutant DNA in cancer patients," Current Opinion in Oncology, vol. 19, pp. 36-42, (2007).

Diekema et al., "Look before You Leap: Active Surveillance forMultidrug-Resistant Organisms," Healthcare Epidemiology• CID 2007:44, pp. 1101-1107 (Apr. 15), electronically published Mar. 2, 2007.

Ding et al., "Direct molecular haplotyping of long-range genomic DNA with M1-PCR," PNAS, vol. 100, No. 13, pp. 7449-7453, Jun. 24, 2003.

Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.

Dressman et al., "Transforming single DNA molecules into fluorescent magnetic particles for detection and enumeration of genetic variations," PNAS, vol. 100, No. 15, Jul. 22, 2003.

Drmanac, et al., Human genome sequencing using unchained base reads on self-assembling DNA nanoarrays. Science. Jan. 1, 2010;327(5961):78-81. Epub Nov. 5, 2009.

(56) References Cited

OTHER PUBLICATIONS

Dube et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Emerson et al., "Microfluidic Modelling Activities at C3M," Centre for Microfluidics & Microsystems Modelling, Daresbury Laboratory, pp. 1-26, May 15, 2006.
Fan et al., "Highly parallel genomic assays," NatureReviews/Genetics, vol. 7, pp. 632-644, Aug. 2006.
Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Fielden et al., "Micro-Droplet Technology for High ThroughoutSystems and Methods," 1 pg., Mar. 8, 2006.
Garaj, et al., Graphene as a subnanometre trans-electrode membrane. Nature. Sep. 9, 2010;467(7312):190-3. Epub Aug. 18, 2010.
Garstecki et al., "Formation of droplets and bubbles in a microfluidic T-junction-scaling and mechanism ofbreak-up," Lab on a Chip, vol. 6, pp. 437-446, (2006).
Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Garti et al., "Water Solubilization in Nonionic Microemulsions Stabilized by Grafted Siliconic Emulsifiers," Journal of Colloid and Interface Science vol. 233,pp. 286-294, (2001).
Gasperlin et al., "The structure elucidation of semisolid w/o emulsion systems containing silicone surfactant," International Journal of Pharmaceutics107,pp. 51-56, (1994).
Ge et al., "Emulsion PCR-based method to detect Y chromosome microdeletions," Analytical Biochemistry, vol. 367, pp. 173-178,May 10, 2007.
Ghenciu et al., "Affinity Extraction into Carbon Dioxide. 1. Extraction of Avidin Using a Biotin-Functional Fluoroether Surfactant," Ind. Eng. Chern. Res. vol. 36, No. 12, pp. 5366-5370, Dec. 1, 1997.
Glotsos et al., "Robust Estimation ofBioaffinity Assay Fluorescence Signals," IEEE Transactions on Information Technology in Biomedicine, vol. 10, No. 4, pp. 733-739, Oct. 2006.
Griffiths et al., "Miniaturising the laboratory in emulsion droplets," TRENDS in Biotechnology, vol. 24, No. 9, pp. 395-402, Jul. 14, 2006.
Gullberg et al., "Cytokine detection by antibody-based proximity ligation," PNAS, vol. 101, No. 22, pp. 8420-8424, Jun. 1, 2004.
Guo et al., "Enhanced discrimination of single nucleotide polymorphisms by artificial mismatch hybridization," Nature Biotechnology vol. 15, pp. 331-335, Apr. 1997.
Gurrieri, et al., Purification and staining of intact yeast DNA chromosomes and real-time observation of their migration during gel electrophoresis. Biochem J. Aug. 15, 1997;326 (Pt 1):131-8.
Gustafsdottir et al., "In vitro analysis of DNA-protein interactions by proximity ligation," PNAS, vol. 104, No. 9, pp. 3067-3072, Feb. 27, 2007.
Harris, et al., Single-molecule DNA sequencing of a viral genome. Science. Apr. 4, 2008;320(5872):106-9.
Higuchi et al., "Kinetic PCR Analysis: Real-time Monitoring of DNA Amplification Reactions," Bio/Technology vol. II, pp. 1026-1030, Sep. 11, 1993.
Hill, R., "Silicone surfactants—new developments," CurrentOpinion in Colloid & Interface Science 7, pp. 255-261, (2002).
Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Holtze et al., "Biocompatible surfactants for water-in-fluorocarbon emulsions," Lab on a Chip, vol. 8, pp. 1632-1639, Sep. 2, 2008.
Hori et al., "Uniform amplification of multiple DNAs by emulsion PCR," Biochemical and Biophysical Research Communications, vol. 352, pp. 323-328, (2007).
Hung et al., "Rapid microfabrication of solvent-resistant biocompatible microfluidic devices," Lab on a Chip, vol. 8, pp. 983-987, Apr. 8, 2008.
Jarvius et al., "Digital quantification using amplified single-molecule detection," Nature Methods, vol. 3, No. 9, pp. 15 pgs, Sep. 2006.
Jiaqi Huang et al., "Rapid Screening of Complex DNA Samples by Single-Molecule Amplification and Sequencing," PLoS ONE, vol. 6, Issue 5, pp. 1-4, May 2011.
Jin et al., "Practical Time-Gated Luminescence Flow Cytometry. II: Experimental Evaluation Using UV LED Excitation," Cytometry Part A• 71A, pp. 797-808, Aug. 24, 2007.
Kalinina et al., "Nanoliter scale PCR with TaqMan Detection," Nucleic Acids Research, vol. 25, No. 10 pp. 1999-2004, (1997).
Katsura et al., "Indirect micromanipulation of single molecules in water-in-oil emulsion," Electrophoresis, vol. 22, pp. 289-293, (2001).
Kekevi et al., Synthesis and Characterization of Silicone-BasedSurfactants as Anti-Foaming Agents, J. Surfact Deterg (2012), vol. 15, pp. 73-81, published online Jul. 7, 2011.
Kiss, et al. High-throughput quantitative polymerase chain reaction in picolitre droplets. Anal Chem. Dec. 1, 2008;80(23):8975-81.
Kojima et al., "PCR amplification from single DNA molecules on magnetic beads in emulsion: application for high-throughput screening of transcription factor targets," Nucleic Acids Research, vol. 33, No. 17, pp. 1-9, (2005).
Kovacic, et al., Protection of megabase DNA from shearing. Nucleic Acids Res. Oct. 11, 1995;23(19):3999-4000.
Kumaresan et al., "High-Throughput Single Copy DNA Amplification and Cell Analysis in Engineered Nanoliter Droplets," Analytical Chemistry, 17 pgs., Apr. 15, 2008.
Kunieda et al., "Effect of Hydrophilic- and Hydrophobic-Chain Lengths on the Phase Behavior of A-B-type Silicone Surfactants in Water," J. Phys. Chern. B, vol. 105, No. 23, pp. 5419-5426, (2001).
Landegren et al., "Padlock and proximity probes for in situ and array-based analyses: tools for the post-genomic era," Comp. Funct. Genom, vol. 4, pp. 525-530, (2003).
Leamon et al., "Overview: methods and applications for droplet compartmentalization ofbiology," Nature Methods, vol. 3, No. 7, pp. 541-543, Jul. 2006.
Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Link et al., "Electric Control of Droplets in MicrofluidicDevices," Angewandte Chemie Int. Ed., vol. 45, pp. 2556-2560, (2006).
Liu et al., "Droplet-based synthetic method using microflow focusing and droplet fusion," Microfluid Nanfluid, vol. 3, pp. 239-243, (2007), published online Sep. 22, 2006.
Lo et al., "Digital PCR for the molecular detection of fetal chromosomal aneuploidy," PNAS, vol. 104, No. 32, pp. 13116-13121, Aug. 7, 2007.
Luk et al., "Pluronic Additives: A Solution to Sticky Problems in Digital Microfluidics," Langmuir, vol. 24, No. 12, pp. 6382-6289, May 16, 2008.
Marguiles, et al., Genome sequencing in microfabricated high-density picolitre reactors. Nature. Sep. 15, 2005;437(7057):376-80. Epub Jul. 31, 2005.
Markey et al., "High-throughput droplet PCR," Methods, vol. 50, pp. 277-281, Feb. 2, 2010.
Mazutis et al., "A fast and efficient microfluidic system for highly selective one-to-one droplet fusion," Lab on a Chip, vol. 9, pp. 2665-2672, Jun. 12, 2009.
Mazutis, et al. Droplet-based microfluidic systems for high-throughput amplification and analysis. Analytical Chemistry, American Chemical Society. 2009; 81(12):4813-4821.
McCaughan et al., "Single-molecule genomics," Journal ofPathology, vol. 220, pp. 297-306, Nov. 19, 2009.
Mehta et al., "Mechanism of Stabilization of Silicone Oil—WaterEmulsions Using Hybrid Siloxane Polymers," Langmuir, vol. 24, No. 9, pp. 4558-4563, Mar. 26, 2008.
Mohr et al., "Numerical and experimental study of a droplet-based PCRchip," Microfluid Nanofluid, vol. 3, pp. 611-621, (2007).
Musyanovych et al., "Miniemulsion Droplets as Single MoleculeNanoreactors for Polymerase Chain Reaction," Biomacromolecules, vol. 6, No. 4, pp. 1824-1828, (2005).

(56) References Cited

OTHER PUBLICATIONS

Nagai et al., "Development of a Microchamber Array forPicoliter PCR," Analytical Chemistry, vol. 73, No. 5, pp. 1043-1047, Mar. 1, 2001.
Nam et al., "Nanosized Emulsions Stabilized by SemisolidPolymer Interphase," Langmuir, ACS Publications, Jul. 23, 2010.
Newman et al., "Phase Behavior ofFluoroether-Functional Amphiphiles in Supercritical Carbon Dioxide," The Journal of Supercritical Fluids, vol. 6, No. 4, pp. 205-210, (1993).
Nie et al., "Optical Detection of Single Molecules," Annu. Rev. Biophys. BiomoL Struct. vol. 26, pp. 567-596, (1997).
O'Lenick, Jr., A.J., "Silicone Emulsions and Surfactants," Journal ofSurfactants and Detergents, vol. 3, No. 3, Jul. 2000.
O'Lenick, Jr., Anthony J., "Silicone Emulsions and Surfactants—A Review," Silicone Spectator, Silitech LLC, May 2009 (original published May 2000).
Pamme, "continuous flow separations in microfluidic devices," Lab on a Chip, vol. 7, pp. 1644-1659, Nov. 2, 2007.
Piatyszek et al., "Detection of telomerase activity in human cells and tumors by a telomeric repeat amplification protocol (TRAP)," Methods in Cell Science 17, pp. 1-15, (1995).
Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Pohl et al., "Principle and applications of digital PCR" review, www.future-drugs.com, Expert Rev. Mol. Diagn. 4(1), pp. 41-47, (2004).
Price, C.B., "Regular Review Point of Care Testing," BMJ, vol. 322, May 26, 2001.
Qin, et al. Studying copy number variations using a nanofluidic platform. Nucleic Acids Res. Oct. 2008;36(18):e116.
Redon, et al., Global variation in copy number in the human genome. Nature. Nov. 23, 2006;444(7118):444-54.
Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Rutledge et al., "Mathematics of quantitative kinetic PCR and the application of standard curves," Nucleic Acids Research, vol. 31, No. 16, pp. 1-6, (2003).
Rutledge, R.G., "Sigmoidal curve-fitting redefines quantitative real-time PCR with the prospective of developing automated high-throughput applications," Nucleic Acids Research. vol. 32, No. 22, pp. 1-8, (2004).
Schneegab et al., "Miniaturized flow-through PCR with different template types in a silicon chip thermocycler," Lab on a Chip, vol. 1, pp. 42-49, (2001).
Schroeder et al., "Introduction to Flow Cytometry" version 5.1,182 pgs. (2004).
Schutze et al., "A streamlined protocol for emulsion polymerase chain reaction and subsequent purification," Analytical Biochemistry, vol. 410, pp. 155-157, Nov. 25, 2010.
Sela et al., "Newly designed polysiloxane-graft-poly (oxyethylene) copolymeric surfactants: preparation, surface activity and emulsification properties," Colloid & Polymer Science 272, pp. 684-691, (1994).
Shah et al., "Polymers fit for function Making emulsions drop by drop," Materials Today, vol. 11, No. 4, pp. 18-27, Apr. 2008.
Shendure et al., "Next-generation DNA sequencing," NatureBiotechnology, vol. 26, No. 10, pp. 1135-1145, Oct. 2008.
Shuber et al., "A Simplified Procedure for Developing Multiplex PCRs," Genome Research, published by Cold Spring Harbor Laboratory Press, pp. 488-493, (1995).
Sigma-Aldrich, "Synthesis ofMesoporous Materials," Material Matters,3.1, 17, (2008).
Singley et al., "Phase behavior and emulsion formation of novel fluoroether amphiphiles in carbon dioxide," Fluid Phase Equilibria 128, pp. 199-219, (1997).
Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.
Snow, S.A., "Synthesis and Characterization of Zwitterionic Silicone Sulfobetaine Surfactants," Langmuir, vol. 6, No. 2, American Chemical Society, pp. 385-391, (1990).
Solimini et al., "Recurrent Hemizygous Deletions in CancersMay Optimize Proliferative Potential," Science, vol. 337, pp. 104-109, Jul. 6, 2012.
Soni, et al., Progress toward ultrafast DNA sequencing using solid-state nanopores. Clin Chem. Nov. 2007;53(11):1996-2001. Epub Sep. 21, 2007.
Swillens et al., "Instant evaluation of the absolute initial number of eDNA copies from a single real-time PCR curve," Nucleic Acids Research, vol. 32, No. 6, pp. 1-6, (2004).
Tanner et al., "Simultaneous multiple target detection in real-time loop-mediated isothermal amplification," BioTechniques, vol. 53, pp. 8-19, Aug. 2012.
Taylor, et al., Functional copy-number alterations in cancer. PLoS One. Sep. 11, 2008;3(9):e3179.
Teh et al., "Droplet microfluidics," Lab on a Chip, vol. 8, pp. 198-220, Jan. 11, 2008.
Thurecht et al., "Investigation of spontaneous microemulsion formation in supercritical carbon dioxide using high-pressure NMR," Journal of Supercritical Fluids, vol. 38, pp. 111-118, (2006).
Thurecht et al., "Kinetics of Enzymatic Ring-Opening Polymerization of E:—Caprolactone in Supercritical Carbon Dioxide," Macromolecules, vol. 39, pp. 7967-7972, (2006).
Vogelstein, et al. Digital PCR. Proc Natl Acad Sci U S A. Aug. 3, 1999;96(16):9236-41.
Vulto et al., "Phaseguides: a paradigm shift in microfluidic priming and emptying," Lab on a Chip, vol. 11, No. 9, pp. 1561-1700, May 7, 2011.
Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).
Weaver et al., "Taking qPCR to a higher level: Analysis of CNV reveals the power of high throughput qPCR to enhance quantitative resolution," Methods, vol. 50, pp. 271-276, Jan. 15, 2010.
Weitz, David A., "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Wetmur et al., "Molecular haplotyping by linking emulsion PCR:analysis ofparaoxonase 1 haplotypes and phenotypes," Nucleic AcidsResearch, vol. 33, No. 8, pp. 2615-2619, (2005).
Wetmur, et al., "Linking Emulsion PCR Haplotype Analysis," PCR Protocols, Methods in Molecular Biology, vol. 687, pp. 165-175, (2011).
Williams et al., "Amplification of complex gene libraries by emulsion PCR," Nature Methods, vol. 3, No. 7, pp. 545-550, Jul. 2006.
Yazdi et al., "Highly Carbon Dioxide Soluble Surfactants, Dispersants and Chelating Agents," Fluid Phase Equilibria, vol. 117, pp. 297-303, (1996).
Zhang et al., "Behavioral Modeling and Performance Evaluation ofMicroelectrofluidics-Based PCR Systems Using SystemC," IEEE Transactions on Computer-Aided Design ofIntegrated Circuits and Systems, vol. 23, No. 6, pp. 843-858, Jun. 2004.
Zhang et al., "Miniaturized PCR chips for nucleic acid amplification and analysis: latest advances and future trends," Nucleic Acids Research, vol. 35, No. 13, pp. 4223-4237, Jun. 18, 2007.
Zhao et al., "Microparticle Concentration and Separation by Traveling-Wave Dielectrophoresis (twDEP) for Digital Microfluidics," Journal ofMicroelectromechanical Systems, vol. 16, No. 6, pp. 1472-1481, Dec. 2007.
Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).

(56) References Cited

OTHER PUBLICATIONS

Zhong et al., "Multiplex digital PCR: breaking the one target per color barrier of quantitative PCR," Lab on a Chip, vol. 11, pp. 2167-2174, (2011).
Zimmermann et al., "Digital PCR: a powerful new tool for noninvasive prenatal diagnosis?," Prenatal Diagnosis, vol. 28 pp. 1087-1093, Nov. 10, 2008.
Supplementary European Search Report from EP Appl. No. 12776570, dated Dec. 19, 2014.
Baroud et al.; "An optical toolbox for total control of droplet microfluidics"; *Lab on a Chip*; 7:1029-1033 (2007).
Grasland-Mongrain et al.; "Droplet coalescence in microfluidic devices"; 2003 (31 pages) retrieved from the internet on Jun. 4, 2007 at www.eleves.ens.fr/home/grasland/rapports/stage4.pdf.
Hindson et al.; "High-Throughput Droplet Digital PCR System for Absolute Quantitation of DNA Copy Number"; *Anal. Chem.*; 83(22):8604-8610 (2011).
Kim et al.; "Nanodroplet real-time PCR system with laser assisted heating"; *Optics Express*; 17(1):218-227 (2009).
Turner et al.; "Methods of Genomic Partitioning"; *Ann. Rev. Genomics Human Genetics*; 10(1):263-284 (2009).
Declaration by Serge Saxonov, dated Oct. 31, 2017.
EP Search Report from EP Application 18175708.9 dated Sep. 28, 2018; 7 pages.
Hanson. J.A. et al.; "Nanoscale double emulsions stabilized by single-component block copolypeptides"; *Nature*; vol. 455, No. 7209; Sep. 4, 2008; pp. 85-88.
Schaerli. Y et al.; "The potential of microfluidic water-in-oil droplets in experimental biology"; *Molecular Biosystems*; Royal Society of Chemistry, GB; vol. 5, No. 12; Dec. 1, 2009; pp. 1392-1404.

\* cited by examiner

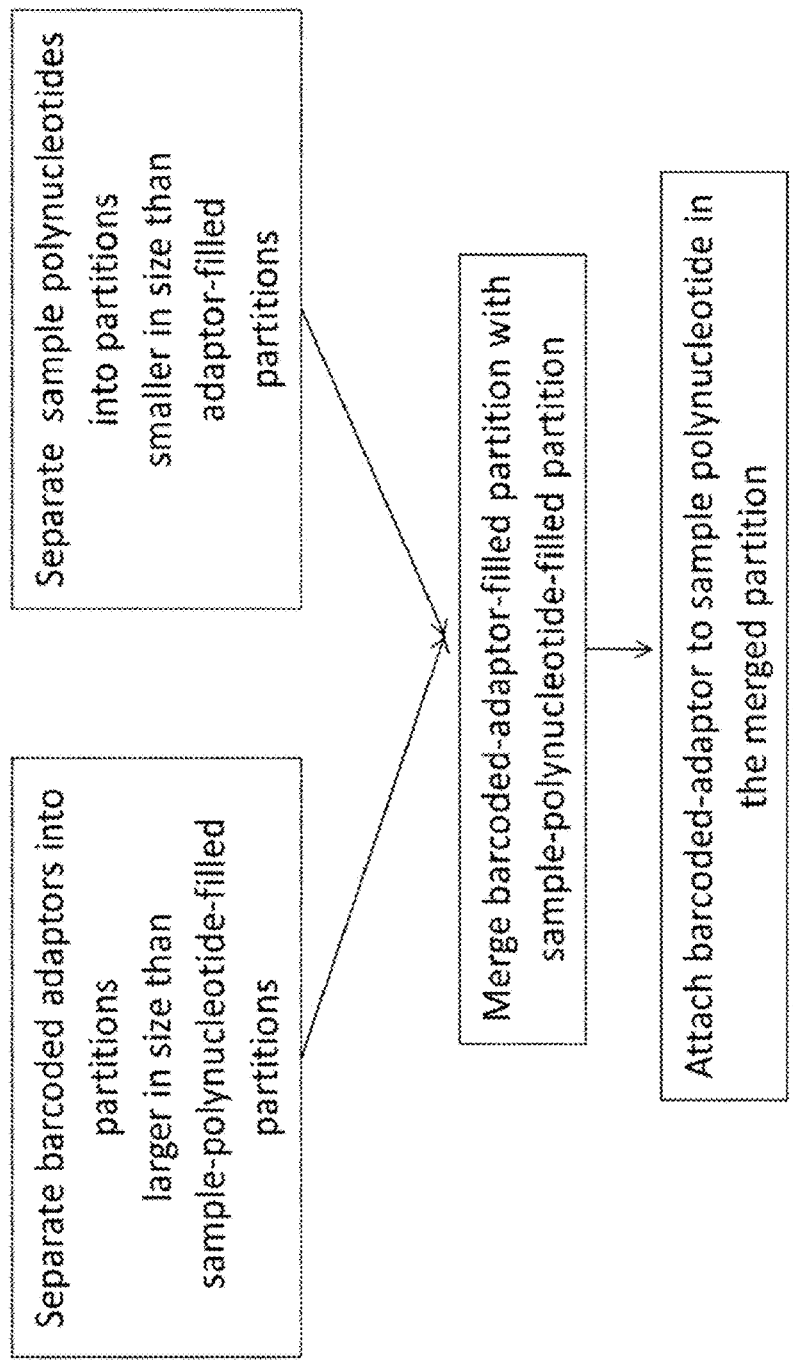

METHODS AND COMPOSITIONS FOR NUCLEIC ACID ANALYSIS

CROSS-REFERENCE TO RELATED APPLICATIONS

This application is a continuation of U.S. patent application Ser. No. 13/456,121, filed on Apr. 25, 2012, which claims the benefit of priority under 35 U.S.C. .§ 119(e) of U.S. Provisional Patent Application No. 61/478,777, filed Apr. 25, 2011, each of which is incorporated herein by reference in its entirety.

BACKGROUND OF THE INVENTION

Next generation sequencing has many useful applications and can be used to analyze multiple samples. There is a need for improved methods of multiplexing samples for applications of next generation sequencing. There is also a need for improved methods of barcode tagging partitioned polynucleotides and analyzing the barcode tagged polynucleotides.

Determining the copy number of a target sequence can have many useful applications. There is a need for improved methods of determining the copy number of a target sequence.

BRIEF SUMMARY OF THE INVENTION

This disclosure provides methods that can be used in sequencing and other applications. In some instances, this disclosure provides a method comprising: a. subdividing a plurality of adaptors into a plurality of first partitions, wherein each of the first partitions has on average a first volume and wherein the adaptors comprise unique barcodes; b. subdividing a sample comprising multiple polynucleotides into a plurality of second partitions, wherein each of the second partitions has on average a second volume, wherein the second volume is greater than the first volume; c. merging at least one of the first partitions with at least one of the second partitions to form a merged partition; and d. tagging one of the multiple polynucleotides, or fragment thereof, with at least one of the adaptors.

The method may comprise: a. subdividing a plurality of adaptors into a plurality of first partitions, wherein each of the first partitions has on average a first volume and wherein the adaptors comprise unique barcodes; b. subdividing a sample comprising multiple polynucleotides into a plurality of second partitions, wherein each of the second partitions has on average a second volume, wherein said second volume is less than said first volume; c. merging at least one of said first partitions with at least one of said second partitions to form a merged partition; and d. tagging one of said multiple polynucleotides, or fragment thereof, with at least one of said adaptors.

Often, in a method disclosed herein, the first partitions are droplets. In some instances, said second partitions are droplets. In some cases, said droplets are within an immiscible fluid.

In some cases, the polynucleotides are genomic DNA. For example, the genomic DNA may be high molecular weight DNA. In some cases, the sample of genomic DNA is partitioned so that it is unlikely that a given partition comprises two or more polynucleotides, or fragments thereof, from the same locus but from different chromosomes.

In some cases, the first partitions are first droplets and the second partitions are second droplets; and prior to the merging, the at least one second droplet comprises the at least one first droplet. In other cases, the first partitions are first droplets and the second partitions are second droplets; and prior to the merging, the at least one second droplet does not comprise the at least one first droplet. In some cases, the first partitions are first droplets and the second partitions are second droplets; and prior to the merging, the at least one first droplet comprises the at least one second droplet. In some cases, the first partitions are first droplets and the second partitions are second droplets; and prior to the merging, the at least one first droplet does not comprise the at least one second droplet.

The volumes of the partitions containing the sample may be different than the volumes of the partitions containing the adaptors. For example, the second volume is at least two times the volume of the first volume. In other cases, the first volume is at least two times the volume of the second volume. The methods disclosed herein may further comprise modifying the temperature of the droplets.

In some cases, the method further comprises merging droplets by a method comprising use of a controller such that each of the first droplets merges with each of the second droplets. In some cases, merging comprises randomly merging droplets comprising polynucleotides with droplets comprising adaptors. The methods may further comprise pooling the adaptor-tagged polynucleotides, or fragments thereof.

Often, the method further comprises analyzing the adaptor-tagged polynucleotides, or fragments thereof. The analyzing may involve sequencing the adaptor-tagged polynucleotides, or fragments thereof. The analyzing may comprise determining whether the adaptor-tagged polynucleotides, or fragments thereof, were located in the same partition; or, in some cases, estimating the likelihood that any two sequence reads generated by the sequencing came from the same or different partitions.

In some cases, the method further comprises fragmenting the polynucleotides within the second partitions to form polynucleotide fragments. The polynucleotides fragments may be generated by fragmenting the polynucleotides with an endonuclease.

In some cases, the polynucleotides are tagged by ligating the adaptors to the polynucleotides within a plurality of the merged partitions. The tagging may be accomplished by multiple means; for example, tagging can be accomplished using transposons.

Often, the methods herein include an amplification reaction. Often, the amplification comprises a polymerase chain reaction; or, the amplification can be a different type of reaction such as multiple-displacement amplification. Often, tagged polynucleotides are amplified; and, in some cases, they are amplified before tagging.

In some cases, each of the first partitions comprises, on average, less than five adaptors. Often, each of said second partitions comprises, on average, less than five of the multiple polynucleotides. In some cases, the subdividing of the sample comprises emulsifying or mixing the sample with the second partitions. Often, the subdividing of the plurality of adaptors comprises emulsifying or mixing the plurality of adaptors with the second partitions.

In some aspects, this disclosure provides a method comprising: a. partitioning organelles into a plurality of partitions, wherein each partition comprises on average less than five organelles per partition; b. lysing the extracellular organelles in the plurality of partitions, wherein the lysing releases RNA from the organelles; c. generating tagged cDNA from the released RNA in the plurality of partitions with adaptors comprising a barcode, wherein each partition in the plurality of partitions comprises adaptors with a unique barcode. In some cases, the organelles are extracellular organelles such as exosomes. In some cases, the generating tagged cDNA comprises reverse transcription of the released RNA with partition-specific barcoded primers. The method may further comprise sequencing the tagged cDNA and/or determining if the tagged cDNA is from the same organelle.

This disclosure also provides a method comprising: a. partitioning microorganisms into a plurality of partitions, b. obtaining polynucleotides from the microorganisms in the plurality of partitions; and c. tagging the polynucleotides in the plurality of partitions with adaptors comprising a barcode, wherein each partition in the plurality of partitions comprises adaptors with a unique barcode. In some cases, each of said partitions comprises, on average, less than five microorganisms. The method may further comprise sequencing the tagged polynucleotides and/or determining if the tagged polynucleotide fragments are from the same partition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features are set forth with particularity in the appended claims. A better understanding of the features and advantages will be obtained by reference to the following detailed description that sets forth illustrative embodiments, in which principles are utilized, and the accompanying drawings of which:

FIGS. 1A and 1B illustrate methods of merging droplets comprising a sample with droplets comprising adaptors with barcodes.

DETAILED DESCRIPTION OF THE INVENTION

In general, described herein are methods, compositions, and kits for library preparation for sequencing polynucleotides. The methods, compositions, and kits can be used to separate a sample of polynucleotides into a plurality of partitions, and each of the plurality of partitions can be provided with a unique set of adaptors comprising a barcode. Library preparation can be performed in each of the plurality of partitions (e.g., droplets). The contents of the partitions can be pooled and sequenced to generate sequence reads, and the barcodes can be used to identify which sequence reads came from the same partition. A number of embodiments of methods, compositions, systems, and kits are provided herein.

Overview

In general, barcoding (or "tagging") can enable one to pool samples of nucleic acids in order to reduce the cost of sequencing per sample, yet retain the ability to determine from which sample a sequence read is derived. Separate library preparations can be prepared for each sample, and each sample can have its own unique barcode. The separately prepared libraries with unique barcodes can then be pooled and sequenced. Each sequence read of the resulting dataset can be traced back to an original sample via the barcode in the sequence read.

In methods provided herein, polynucleotides in a sample can be separated into a plurality of partitions, e.g., droplets. Adaptors with a unique barcode (or "tag") can be supplied to each of a plurality of partitions comprising polynucleotides. Polynucleotides with barcode adaptors can be sequenced, and the barcodes can be used determine if two or more sequence reads were generated from one or more polynucleotides in the same partition.

Figure 1A:
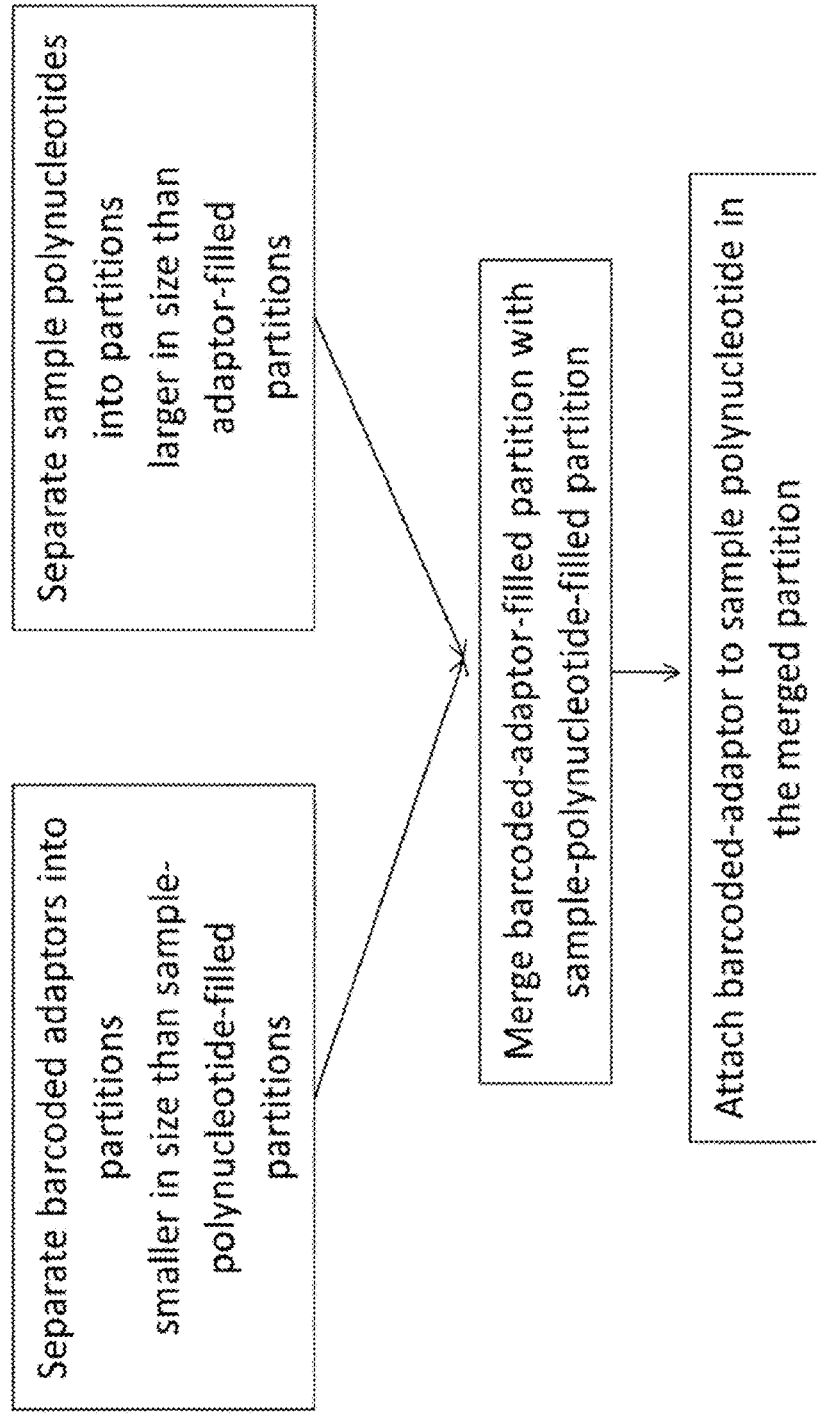

Barcode adaptors can be bundled within a partition, e.g., an aqueous phase of an emulsion, e.g., a droplet. Barcode tagging may be accomplished by merging adaptor-filled partitions (e.g., droplets) with sample-polynucleotide-containing partitions (e.g., droplets). In some cases, adaptor-filled partitions are smaller than sample-polynucleotide-containing partitions (see e.g., FIG. 1A). Barcoded-adaptors can be separated into a plurality of partitions smaller in size than sample-polynucleotide-containing partitions. Larger sample-polynucleotide-containing partitions can be formed. A barcoded-adaptor-filled partition can be merged with a sample-polynucleotide-containing partition, and an adaptor can be attached to a polynucleotide. For example, the partitions containing sample polynucleotide may be, on average, greater than 1.5-fold, 2-fold, 2.5-fold, 3-fold, 3.5-fold, 4-fold, 4.5 fold, 5-fold, 6-fold, 7-fold, 8-fold, 9-fold, 10-fold, 20-fold, 50-fold, 75-fold, 100-fold, 500-fold, 1000-fold, 10,000-fold, 50,000-fold, or 100,000-fold the average size the of the partitions containing the adaptors. The partitions containing sample polynucleotide may be, on average, greater than 1.5-fold, 2-fold, 2.5-fold, 3-fold, 3.5-fold, 4-fold, 4.5 fold, 5-fold, 6-fold, 7-fold, 8-fold, 9-fold, 10-fold, 20-fold, 50-fold, 75-fold, 100-fold, 500-fold, 1000-fold, 10,000-fold, 50,000-fold, or 100,000-fold the average volume of the partitions containing the adaptors. In some cases, sample-polynucleotide-containing partitions are formed so that they contain adaptor-filled partitions. For example, adaptor-filled partitions (e.g., droplets) can be emulsified with a polynucleotide sample so that sample-polynucleotide-containing partitions (e.g., droplets) end up containing adaptor-filled partitions. The adaptor-filled droplets can be burst (e.g., through a temperature adjustment) to release reaction components (e.g., PCR or ligation components) that can be used for library preparation. In some embodiments, the temperature adjustment comprises raising the temperature to about, more than about, or at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. for about, more than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 min. In some embodiments, the temperature adjustment can last for about, more than about, or at least about 1, 2, 3, 4, 5, 6, 7, 8, 9, 10, 11, 12, 13, 14, 15, 16, 17, 18, 19, 20, 21, 22, 23, or 24 hrs. In some cases, the adaptor-filled droplets are not contained within the sample-containing droplets. In such cases, separate droplets may be merged together.

In some cases, an adaptor-filled partition is larger than a sample-polynucleotide-containing partition (see e.g., FIG. 1B). Barcoded-adaptors can be separated into a plurality of partitions larger in size than sample-polynucleotide-containing partitions. Smaller sample-polynucleotide-containing partitions can be formed. A barcoded-adaptor-filled partition can be merged with a sample-polynucleotide-containing partition, and an adaptor can be attached to a polynucleotide. For example, partitions containing adaptors may be, on average, greater than 1.5-fold, 2-fold, 2.5-fold, 3-fold, 3.5-fold, 4-fold, 4.5 fold, 5-fold, 6-fold, 7-fold, 8-fold, 9-fold, 10-fold, 20-fold, 50-fold, 75-fold, 100-fold, 500-fold, 1000-fold, 10,000-fold, 50,000-fold, or 100,000-fold the average size of the partitions containing the samples. The partitions containing adaptors can be, on average, greater than 1.5-fold, 2-fold, 2.5-fold, 3-fold, 3.5-fold, 4-fold, 4.5 fold, 5-fold, 6-fold, 7-fold, 8-fold, 9-fold, 10-fold, 20-fold, 50-fold, 75-fold, 100-fold, 500-fold, 1000-fold, 10,000-fold, 50,000-fold, or 100,000-fold the average volume of the partitions containing the samples. In some cases, adaptor-containing partitions are formed so that they contain sample-containing partitions. For example, in some embodiments, sample-polynucleotide-filled partitions (e.g., droplets) can be emulsified with adaptors so that adaptor-containing partitions (e.g., droplets) end up enveloping sample-containing partitions. In such cases, the sample-containing droplets can be burst (e.g., through a temperature adjustment) so that the contents of the different types of droplets can merge. In some embodiments, the temperature adjustment comprises raising the temperature to about, more than about, or at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. for about, more than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 min. In some embodiments, the temperature adjustment can last for about, more than about, or at least about 1, 2, 3, 4, 5, 6, 7, 8, 9, 10, 11, 12, 13, 14, 15, 16, 17, 18, 19, 20, 21, 22, 23, or 24 hrs. In some cases, the sample-polynucleotide-filled droplets are not contained within the adaptor-containing droplets. In such cases, separate droplets may be merged together.

A microfluidic device can be used to merge pre-made adaptor reagents with a plurality of sample-polynucleotide partitions such that every sample-polynucleotide partition comprises adaptor reagents. For example, a square-shaped device can be used with 1000×1000 (one million) partitions, and each polynucleotide can be tagged with two barcodes. One million unique identifiers can be constructed with 2,000 different barcodes. Reagents with 1,000 different barcodes can be loaded in horizontal channels of the device and reagents for another set of 1,000 different barcodes can be loaded in vertical channels of the device. Every one of the million partitions can have its own unique combination of barcodes.

In some cases, sample-polynucleotide-containing partitions (e.g., droplets) and adaptor-filled partitions (e.g., droplets) are merged in a controlled manner, e.g., one droplet of sample polynucleotides with one droplet of unique adaptors. In some cases, adaptor-filled partitions are randomly merged with sample-polynucleotide-containing partitions.

The following example illustrates an embodiment of a method. A large set of droplets of a number (N) types can be made. Each type of droplet can be loaded with its own barcode. The value N can be determined in part by the length of the barcode (L). For example, N can be as large as 4 L. Thus, if L=10, around 1 million different droplet types can be generated. Standard sequencing library preparation within each partition can be performed. Once the libraries are prepared, the contents of all the partitions can be merged (e.g., by breaking droplets) and loaded onto a nucleic acid sequencer. The sequencer can generate sequence reads for many of the library polynucleotides. Polynucleotides prepared within the same droplet can contain the same barcode. If the number of barcodes is sufficiently large, it can be surmised that molecules containing the same barcode came from the same partition. If N is sufficiently large (e.g., larger than the number of adaptor-filled partitions actually used in the experiment), it can be expected that any two sample-polynucleotide-containing partitions can be tagged by different adaptor-filled partitions. However, if N is not very large, sample-polynucleotide partitions can be tagged with the same adaptors. In that case, the likelihood that any two reads came from the same or different sample containing partitions can be estimated probabilistically. For many applications, a probabilistic assessment can be sufficient.

In some embodiments, the number of different samples that can be multiplexed, e.g., in a sequencing reaction, can be about, more than about, less than about, or at least about 1000, 5000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, or 10,000,000 samples. In some embodiments, about 1000 to about 10,000, about 10,000 to about 100,000, about 10,000 to about 500,000, about 100,000 to about 500,000, about 100,000 to about 1,000,000, about 500,000 to about 1,000,000, about 1,000,000 to about 5,000,000, or about 1,000,000 to about 10,000,000 samples are multiplexed in the methods described herein.

Some methods of barcode tagging are described, for example, in U.S. Patent Application Publication No. 20110033854.

Fusing Smaller Droplets (E.g., Inner Droplets) with Larger Droplets (E.g., Outer Droplets)

Some methods for fusing smaller droplets (e.g., inner droplets) with larger droplets (e.g., outer droplets) are disclosed, e.g., in U.S. Patent Application Publication No. 20110053798. In some cases, an inner droplet (or partition) can be fused with an outer droplet (or partition) by heating/cooling to change temperature, applying pressure, altering composition (e.g., via a chemical additive), applying acoustic energy (e.g., via sonication), exposure to light (e.g., to stimulate a photochemical reaction), applying an electric field, or any combination thereof. In some cases, the inner droplet may fuse to the outer droplet spontaneously. The treatment may be continuous or may vary temporally (e.g., pulsatile, shock, and/or repetitive treatment). The treatment may provide a gradual or rapid change in an emulsion parameter, to effect steady state or transient initiation of droplet fusion. The stability of the partitions, and their responsiveness to a treatment to induce droplet fusion, may be determined during their formation by selection of an appropriate surfactant type, surfactant concentration, critical micelle concentration, ionic strength, etc., for one or more phases of the inner/outer partition.

The fusing can result in a fused emulsion. Fusion may occur spontaneously, such that no treatment, other than a sufficient time delay (or no delay), is necessary before processing fused droplets. Alternatively, the inner/outer droplet may be treated to controllably induce fusion of droplets to form assay mixtures.

The fused emulsion may be processed. Processing may include subjecting the fused emulsion to any condition or set of conditions under which at least one reaction of interest can occur (and/or is stopped), and for any suitable time period. Accordingly, processing may include maintaining the temperature of the fused emulsion near a predefined set point, varying the temperature of the fused emulsion between two or more predefined set points (such as thermally cycling the fused emulsion), exposing the fused emulsion to light, changing a pressure exerted on the fused emulsion, adding at least one chemical substance to the fused emulsion, applying an electric field to the fused emulsion, or any combination thereof, among others.

Signals may be detected from the fused emulsion after and/or during processing. Detection is described further in other sections herein. The signals may be detected optically, electrically, chemically, or a combination thereof, among others. The detected signals may include test signals that correspond to at least one reaction of interest performed in the fused emulsion. Alternatively, or in addition, the detected signals may include code signals that correspond to codes present in the fused emulsion. Test signals and code signals generally are distinguishable and may be detected using the same or distinct detectors. For example, the test signals and code signals each may be detected as fluorescence signals, which may be distinguishable based on excitation wavelength (or spectrum), emission wavelength (or spectrum), and/or distinct positions in a fused droplet (e.g., code signals may be detectable as more localized than test signals with respect to fused droplets), among others. As another example, the test signals and code signals may be detected as distinct optical characteristics, such as test signals detected as fluorescence and code signals detected as optical reflectance. As a further example, the test signals may be detected optically and the code signals electrically, or vice versa.

Adaptors

Barcodes can be present on adaptors, and an adaptor with a barcode can be attached to a polynucleotide by ligation. A variety of types of adaptors can be used in the methods, compositions, systems, and kits described herein. For example, an adaptor can comprise double stranded sequence. An adaptor with double stranded sequence can comprise one blunt end. In some cases, an adaptor with double stranded sequence comprises two blunt ends. An adaptor with double stranded sequence can comprise one 3' overhang. An adaptor with double stranded sequence can comprise two 3' overhangs. An adaptor with double stranded sequence can comprise one 5' overhang. In some cases, an adaptor with double stranded sequence can comprise two 5' overhangs. An adaptor with double stranded sequence can comprise a 5' overhang and a 3' overhang. In some cases, an adaptor comprises only single stranded nucleic acid.

When an adaptor has one or more overhangs, the overhang can be about, more than about, less than about, or at least about 1, 2, 3, 4, 5, 6, 7, 8, 9, 10, 11, 12, 13, 14, 15, 16, 17, 18, 19, or 20 bases. For example, a 3' overhang can be about, more than about, less than about, or at least about 1, 2, 3, 4, 5, 6, 7, 8, 9, 10, 11, 12, 13, 14, 15, 16, 17, 18, 19, or 20 bases. A 5' overhang can be about, more than about, at least about, or less than about 1, 2, 3, 4, 5, 6, 7, 8, 9, 10, 11, 12, 13, 14, 15, 16, 17, 18, 19, or 20 bases. If an adaptor comprises two overhangs, the overhangs can comprise the same or different number of bases.

The longest strand of an adaptor can be about, more than about, less than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 bases. If an adaptor comprises a double-stranded portion, the double stranded portion can be about, more than about, at least about, or less than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base-pairs.

An adaptor can comprise DNA and/or RNA. In some cases, an adaptor comprises DNA. In some cases, an adaptor comprises RNA. In some cases, an adaptor comprises DNA and RNA.

An adaptor can comprise double stranded nucleic acid. In some cases, an adaptor comprises double stranded DNA. In some cases, an adaptor comprises double stranded RNA. In some cases, an adaptor comprises a DNA/RNA hybrid duplex.

An adaptor can comprise single stranded nucleic acid. In some embodiments, an adaptor comprises single stranded RNA. In some cases, an adaptor comprises single stranded DNA. In some cases, an adaptor comprises single stranded RNA and DNA.

When an adaptor comprises double stranded sequence, one strand of the adaptor can comprise only DNA and one strand of the adaptor can comprise only RNA. A first strand can comprise DNA and RNA and a second strand can comprise DNA only. A first stand can comprise DNA and RNA, and a second strand can comprise RNA only. If a strand of an adaptor comprises both DNA and RNA, the DNA can be 5' of the RNA or the DNA and be 3' or the RNA. In some embodiments, an adaptor is single stranded and comprises DNA and RNA, and the DNA is 5' of the RNA or 3' of the RNA.

An adaptor can comprise a hairpin (or hairpin loop). A hairpin can comprise DNA and/or RNA. The number of nonbase-paired bases in a loop of a hairpin can be about, more than about, or at least about 4, 5, 6, 7, 8, 9, 10, 11, 12, 13, 14, 15, 16, 17, 18, 19, 20, 21, 22, 23, 24, 25, 26, 27, 28, 29, or 30 bases. The number of nonbase-paired bases in a loop of a hairpin can be about 4 to about 8, about 4 to about 10, about 4 to about 14, about 4 to about 16, about 4 to about 20, about 4 to about 24, about 4 to about 26, or about 4 to about 30 bases. The length of the stem (base-paired portion) of the adaptor can be about, more than about, or at least about 4, 5, 6, 7, 8, 9, 10, 11, 12, 13, 14, 15, 16, 17, 18, 19, 20, 21, 22, 23, 24, 25, 26, 27, 28, 29, or 30 base-pairs.

In some cases, a hairpin adaptor is ligated to only one end of a polynucleotide. In some cases, a first hairpin adaptor is ligated to one end of a polynucleotide and a second hairpin adaptor is ligated to the other end of the polynucleotide. The hairpin adaptors that are ligated to each end of a polynucleotide can comprise the same nucleic acid sequence or different nucleic acid sequence. The hairpin adaptors that ligate to each end of a polynucleotide can have barcodes, and the barcodes can be the same or different. A hairpin adaptor that ligates to one end of a polynucleotide can have a barcode, and a hairpin adaptor that ligates to the other end of a polynucleotide can lack a barcode.

In some cases, adaptors are ligated to polynucleotides such that multiple adaptors and polynucleotides are interspersed.

Barcode

An adaptor can comprise one or more barcode (tag) sequences. A barcode sequence can be a unique identifier. In some embodiments, a barcode is about, more than about, less than about, or at least about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases or bases pairs. In some embodiments, a barcode is about 4 to about 6 bases or bp, about 4 to about 7 bases or bp, about 4 to about 8 bases or bp, about 4 to about 9 bases or bp, about 4 to about 10 bases or bp, about 4 to about 12 bases or bp, about 4 to about 14 bases or bp, about 4 to about 16 bases or bp, about 4 to about 18 bases or bp, about 4 to about 20 bases or bp, about 5 to about 10 bases or bp, about 5 to about 15 bases or bp, about 5 to about 20 bases or bp, about 5 to about 25 bases or bp, about 5 to about 30 bases or bp, about 5 to about 35 bases or bp, about 5 to about 40 bases or bp, or about 5 to about 50 bases or bp. In some embodiments, bases in a barcode are contiguous. In some embodiments, bases in a barcode are noncontiguous. In some embodiments, an adaptor comprises no barcodes.

A barcode can be double stranded in an adaptor. In some cases, a barcode is single stranded in an adaptor. A barcode can comprise double stranded and single stranded sequence in an adaptor. An adaptor can comprise about, more than about, at least about, or less than about 1, 2, 3, 4, 5, 6, 7, 8, 9, or different barcodes. If an adaptor comprises more than one barcode, the barcodes can be separated from each other by about, more than about, or at least about 1, 2, 3, 4, 5, 6, 7, 8, 9, 10, 11, 12, 13, 14, 15, 16, 17, 18, 19, or 20 bases or base pairs on the adaptor.

Commercially available kits comprising adaptors with barcodes can be used in the methods described herein. For example, a kit comprising adaptors with barcodes can include the ENCORE™ 384 Multiplex System (NUGEN®) which can comprise 384 molecularly barcoded library adaptors. The ENCORE™ NGS Multiplex Library Systems for ION TORRENT™ can comprise adaptors with barcodes that can be ligated to fragments. The ENCORE™ Complete RNA-Seq IL Multiplex System 1-8 (NUGEN®) and ENCORE™ Complete RNA-Seq IL Multiplex System 9-16 (NUGEN®) can provide barcoded adaptors for multiplex sequencing. The ENCORE™ Complete RNA-Seq DR Multiplex system 1-8 (NUGEN®) and ENCORE™ Complete RNA-Seq DR Multiplex system 9-16 (NUGEN®) can provide a dedicated read (DR) barcode design. Examples of kits with adaptors with barcodes from LIFE TECHNOLOGIES™ include 5500 SOLiD™ Fragment Library Barcode Adaptors 1-16, 5500 SOLiD™ Fragment Library Barcode Adaptors 1-96, 5500 SOLiD™ Fragment Library Barcode Adaptors 17-32, 5500 SOLiD™ Fragment Library Barcode Adaptors 33-48, 5500 SOLiD™ Fragment Library Barcode Adaptors 49-64, 5500 SOLiD™ Fragment Library Barcode Adaptors 65-80, 5500 SOLiD™ Fragment Library Barcode Adaptors 81-96, 5500 SOLiD™ Fragment Library Core Kit, 5500 SOLiD™ Fragment Library Standard Adaptors, LIBRARY BUILDER™ Fragment Core Kit for 5500 Genetic Analysis Systems, SOLiD™ Fragment Library Barcoding Kit 1-96, SOLiD™ Fragment Library Barcoding Kit Module 17-32, SOLiD™ Fragment Library Barcoding Kit Module 33-48, SOLiD™ Fragment Library Barcoding Kit Module 49-64, SOLiD™ Fragment Library Barcoding Kit Module 65-80, SOLiD™ Fragment Library Barcoding Kit Module 81-96, SOLiD™ RNA Barcoding Kit, Module 1-16, SOLiD™ RNA Barcoding Kit, Module 1-48, SOLiD™ RNA Barcoding Kit, Module 1-96, SOLiD™ RNA Barcoding Kit, Module 17-32, SOLiD™ RNA Barcoding Kit, Module 33-48, SOLiD™ RNA Barcoding Kit, Module 49-64, SOLiD™ RNA Barcoding Kit, Module 49-96, SOLiD™ RNA Barcoding Kit, Module 65-80, or SOLiD™ RNA Barcoding Kit, Module 81-96.

Other commercially available kits with adaptors with barcodes include SureSelect AB Barcode Adaptor Kit (AGILENT TECHONOLOGIES), Bioo Scientific's AIR™ Barcoded Adapters, NEXTFLEX™ DNA Barcodes, ILLUMINA® TRUSEQ™ RNA and DNA Sample Preparation Kits, RAINDANCE® Technologies DEEPSEQ™ FFPE solution, NEBNEXT® Multiplex Oligos for ILLUMNIA® (Index Primers 1-12), or NEBNEXT® Multiplex Small RNA Library Prep set for ILLUMNIA® (Index Primers 1-12).

A polynucleotide can receive a barcode by being ligated to an adaptor comprising a barcode. The ligation can involve use of one or more ligases. A barcode can be attached to a polynucleotide by amplification with a primer comprising a barcode.

A barcode can be adjacent to a primer binding site. A barcode can be 0 or about 1, 2, 3, 4, 5, 6, 7, 8, 9, 10, 11, 12, 13, 14, 15, 16, 17, 18, 19, or 20 bases 3' of a primer binding (annealing, hybridization) site.

Primer/Probe Binding Site

An adaptor can comprise one or more primer, probe, or oligonucleotide hybridization sites. The one or more primer, probe, or oligonucleotide hybridization sites can be about, more than about, less than about, or at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases. A primer, probe, or oligonucleotide hybridization site can be used to anneal an oligonucleotide primer to the adaptor for amplification or to anneal a primer to the adaptor for a sequencing reaction. An adaptor can comprise sequence for annealing of more than one oligonucleotide primer or probes, e.g., 2, 3, 4, 5, 6, 7, 8, 9, 10 or more oligonucleotide primers or probes. An adaptor can have a site for annealing a sequencing primer and an amplification primer. A primer or probe that anneals to an adaptor can be about, more than about, less than about, or at least about 8, 9, 10, 11, 12, 13, 14, 15, 16, 17, 18, 19, 20, 21, 22, 23, 24, 25, 26, 27, 28, 29, or 30 bases in length.

Restriction Enzyme Site

An adaptor can comprise one or more restriction enzyme binding sites and or cleavage sites. A restriction enzyme that can bind or cleave an adaptor can be, e.g., AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166I, Hpy188I, Hpy188 III, Hpy99I, HpyAV, HpyCH4III, HpyCH41V, HpyCH4V, KasI, KpnI, MboI, MboII, MfeI, MluI, MlyI, MmeU, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PfIFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Taq.alpha.I, TfiI, TliI, TseI, Tsp45I, Tsp509I, TspMI, TspRI, Tth11I, XbaI, XcmI, XhoI, XmaI, XmnI, or ZraI.

An adaptor can comprise a Type IIS restriction enzyme binding site. A Type IIS restriction enzyme can cleave DNA at a defined distance from a non-palindromic asymmetric recognition site. Examples of Type IIS restriction enzymes include AarI, Acc36I, AccBSI, AciI, AclWI, AcuI, AloI, Alw26I, AlwI, AsuHPI, BaeI, BbsI, BbvCI, BbvI, BccI, BceAI, BcgI, BciVI, BfiI, BfuAI, BfuI, BmgBI, BmrI, BpiI, BpmI, Bpu10I, Bpu10I, BpuAI, BpuEI, BsaI, BsaMI, BsaXI, BseII, Bse3DI, BseGI, BseMI, BseMII, BseNI, BseRI, BseXI, BseYI, BsgI, BsmAI, BsmBI, BsmFI, BsmI, Bso31I, BspCNI, BspMI, BspQI, BspTNI, BsrBI, BsrDI, BsrI, BsrSI, BssSI, Bst2BI, Bst6I, BstF5I, BstMAI, BstV1I, BstV2I, BtgZI, BtrI, BtsCI, BtsI, CspCI, Eam1104I, EarI, EciI, Eco31I, Eco57I, Eco57MI, Esp3I, FauI, FauI, FokI, GsuI, HgaI, Hin4I, HphI, HpyAV, Ksp632I, LweI, MbiI, MboII, MlyI, MmeI, MnlI, Mva1269I, NmeAIII, PctI, PleI, PpiI, PpsI, PsrI, SapI, SchI, SfaNI, SmuI, TspDTI, TspGWI, or Taq II. A restriction enzyme can bind recognition sequence within an adaptor and cleave sequence outside the adaptor (e.g., in a polynucleotide).

The restriction enzyme can be a methylation sensitive restriction enzyme. The methylation sensitive restriction enzyme can specifically cleave methylated DNA. The methylation sensitive restriction enzyme can specifically cleave unmethylated DNA. A methylation sensitive enzyme can include, e.g., DpnI, Acc65I, KpnI, ApaI, Bsp120I, Bsp143I, MboI, BspOI, NheI, Cfr9I, SmaI, Csp6I, RsaI, Ecl136II, SacI, EcoRII, MvaI, HpaII, MSpJI, LpnPI, FsnEI, DpnII, McrBc, or MspI.

An adaptor can comprise one or more recognition sites for one or more nicking endonucleases, Type I endonucleases, or Type III endonucleases. A nicking endonuclease can hydrolyze only one strand of a duplex to produce DNA molecules that are "nicked" rather than cleaved. The nicking can result in a 3-hydroxyl and a 5'-phosphate. Examples of nicking enzymes include Nt.CviPII, Nb.BsmI, Nb.BbvCI, Nb.BsrDI, Nb.BtsI, Nt.BsmAI, Nt.BspQI, Nt.AlwI, Nt.BbvCI, or Nt.BstNBI. A Type I endonuclease can cleave at a site that differs and is at a random distance away from the recognition site. A Type III endonuclease can recognize two separate non-palindromic sequences that are inversely oriented. Examples of Type III restriction enzymes include EcoP15 and EcoP1.

One or more restriction enzymes used in the methods, compositions and/or kits described herein can be a component of a hybrid or chimeric protein. For example, a domain of a restriction enzyme comprising an enzymatic activity (e.g., endonuclease activity) can be fused to another protein, e.g., a DNA binding protein. The DNA binding protein can target the hybrid to a specific sequence on a DNA. The nucleic acid cleavage activity of the domain with enzymatic activity can be sequence specific or sequence non-specific. For example, the non-specific cleavage domain from the Type IIs restriction endonuclease FokI can be used as the enzymatic (cleavage) domain of the hybrid nuclease. The sequence the domain with the enzymatic activity can cleave can be limited by the physical tethering of the hybrid to DNA by the DNA binding domain. The DNA binding domain can be from a eukaryotic or prokaryotic transcription factor. The DNA binding domain can recognize about, or at least about 2, 3, 4, 5, 6, 7, 8, 9, 10, 11, 12, 13, 14, 15, 16, 17, 18, 19, 20, 21, 22, 23, 24, or 25 bases or base pairs of continuous nucleic acid sequence. The DNA binding domain can recognize about 9 to about 18 bases or base pairs of sequence. The DNA binding domain can be, e.g., a zinc finger DNA binding domain. The DNA binding domain can be from a naturally occurring protein. The DNA binding domain can engineered to specifically bind any desired nucleotide sequence. The hybrid can be a zinc finger nuclease (e.g., zinc finger nuclease). The hybrid protein can function as a multimer (e.g., dimer, trimer, tetramer, pentamer, hexamer, etc.).

Modifications

An adaptor can comprise one or more end modifications. An adaptor can comprise one 5' phosphate. An adaptor can comprise two 5' phosphates. An adaptor can comprise one 3' hydroxyl. An adaptor can comprise two 3' hydroxyls. An adaptor can lack a 3' hydroxyl.

An adaptor can comprise one or more 3' end modifications. The 3' end modification can be, e.g., 3'-amino, 3'-black hole quencher (e.g., BHQ-0, BHQ-1, BHQ-2), 3'-biotin, 3'-chloesterol, 3'-dabcyl CPG, 3' dabsyl CPG, 3'-dye (e.g., fluorescein-CGP, Tamra-CPG, Rox-CPG, Cal Fluor 560-CPG, Quasar 570 (Cy3 substitute)-CGP, Quasar 670 (Cy5 substitute)-CPG, Quasar 705 (Cy5.5 substitute)-CPG, Pulsar 650-CPG, Epoch Richmond Red-CPG, Epoch Yakima Yellow-CPG, Acridine-CPG, 3'-inverted linkage (with 5'-OH attached to support and 3'-OH available for chain extension), 3'-phosphate. An adaptor can comprise any fluorescent dye described herein.

An adaptor can comprise one or more 5' end modifications. The 5' end modification can be, e.g., a 5'-amino group, 5'-biotin, 5'-digoxigenin (DIG), 5' phosphate group, or 5'-thiol. An adaptor can comprise a 5' aldehyde, 5' alkaline phosphatase, 5' amine, 5' horse radish peroxidase (HRP), 5' fluorescein, 5' HEX, 5' ROX, 5' TET, or 5' TAMRA. The 5' modification can be a molecular probe dye, e.g., Alexa Fluor 488, Alexa Fluoro 532, Alexa Fluor 546, Alexa Fluor 555, Alexa Fluor 594, Alexa Fluor 647, Alexa Fluor 660, Alexa Fluor 750, BODIPY® FL, BODIPY® 530/550, BODIPY® 493/503, BODIPY® 558/569, BODIPY® 564/570, BODIPY® 576/589, BODIPY® 581/591, BODIPY® FL-X, BODIPY® TR-X, BODIPY® TMR, BODIPY® R6G, BODIPY® R6G-X, BODIPY® 630/650, BODIPY® 650/665, CASCADE BLUE™ Dye, MARINA BLUE™, OREGON GREEN® 514, OREGON GREEN® 488, OREGON GREEN® 488-X, PACIFIC BLUE™ Dye, RHODAMINE GREEN™ Dye, RHODOL GREEN™ Dye, RHODAMINE GREEN™-X, RHODAMINE RED™-X, TEXAS RED®, or TEXAS RED™-X.

A modification can be attached to a nucleic acid strand through a linker, e.g., C1, C2, C3, C4, C5, C6, C7, C8, C9, C10, C11, C12, C13, C14, C15, C16, C17, C18, C19, or C20. A linker can be, e.g., PC (photo cleavable) spacer, hexanediol, spacer 9 (a triethylene glycol spacer), spacer 18 (an 18-atom hexa-ethyleneglycol spacer), 1',2' dideoxyribose (dspacer), or I-linker (from Exiqon).

An adaptor can comprise one or more methyl groups.

An adaptor can be synthesized with canonical nucleotides (dATP, dCTP, dGTP, and dTTP). An adaptor can be made one or more noncanonical nucleotides. The noncanonical nucleotide can be dUTP. An adaptor can comprise deoxyuracil or deoxyinosine.

An adaptor can comprise one or more RNA-like nucleosides, e.g., ANA (arabino), LNA (locked), 2'-O methyl RNA, FANA (2'-fluoroarabino), or 2'-fluoro RNA. An adaptor can comprise a DNA-like nucleoside, e.g., β-D-DNA, β-L-DNA, or α-D-DNA. An adaptor can comprise one or more 5'-3 phosphorothioate linkages or inverted linkages (5'-5' or 3'-3'). An adaptor can comprise A-phosphorothioate, C-phosphorothioate, G-phosphorothioate, or T-phosphorothioate.

Modified bases in an adaptor can include, e.g., LNA (locked nucleic acid), 2-aminopurine, trimer-20, fluoro bases, 2,6-diaminopurine (2-amino-dA), 5-bromo dU, deoxyuridine, inverted dT, dideoxy C, 5-methyldC, deoxylnosine, 5-nitroindole, ribo A, ribo C, ribo G, ribo U, or –+2' 0-methyl RNA bases. An adaptor can have any type of nucleic acid modification described herein.

In some embodiments, an adaptor is chemically synthesized. In some embodiments, an adaptor is not chemically synthesized.

The modifications described herein can be found on sample polynucleotides.

Partitions

A partition can be formed by any mode of separating that can be used for digital PCR. A partition can be a microfluidic channel, a well on a nano- or microfluidic device or on a microtiter plate, or a reaction chamber in a microfluidic device. A partition can be an area on an array surface. A partition can be an aqueous phase of an emulsion (e.g., a droplet). Methods of generating droplets are described herein.

Droplet Generation

The present disclosure includes compositions, methods, and kits for manipulation of genetic material in droplets, e.g., using droplet digital PCR. The droplets described herein can include emulsion compositions (or mixtures of two or more immiscible fluids) described in U.S. Pat. No. 7,622,280, and droplets generated by devices described in International Application Publication No. WO/2010/036352, first inventor: Colston, each of which is hereby incorporated by reference in its entirety. The term emulsion, as used herein, can refer to a mixture of immiscible liquids (such as oil and water). Oil-phase and/or water-in-oil emulsions can allow for the compartmentalization of reaction mixtures within aqueous droplets. In some embodiments, the emulsions can comprise aqueous droplets within a continuous oil phase. In other embodiments, the emulsions provided herein are oil-in-water emulsions, wherein the droplets are oil droplets within a continuous aqueous phase. The droplets provided herein can be used to prevent mixing between compartments, and each compartment can protect its contents from evaporation and coalescing with the contents of other compartments. One or mote enzymatic reactions can occur in a droplet.

The mixtures or emulsions described herein can be stable or unstable. The emulsions can be relatively stable and have minimal coalescence. Coalescence can occur when small droplets combine to form progressively larger droplets. Less than about 0.00001%, 0.00005%, 0.00010%, 0.00050%, 0.001%, 0.005%, 0.01%, 0.05%, 0.1%, 0.5%, 1%, 2%. 2.5%, 3%, 3.5%, 4%, 4.5%, 5%, 6%, 7%, 8%, 9%, or 10% of droplets generated from a droplet generator can coalesce with other droplets. The emulsions can also have limited flocculation, a process by which the dispersed phase comes out of suspension in flakes.

Splitting a sample into small reaction volumes as described herein can enable the use of reduced amounts of reagents, thereby lowering the material cost of the analysis.

Reducing sample complexity by partitioning can also improve the dynamic range of detection, since higher-abundance molecules can be separated from low-abundance molecules in different compartments, thereby allowing lower-abundance molecules greater proportional access to reaction reagents, which in turn can enhance the detection of lower-abundance molecules.

Droplets can be generated having an average diameter of about, more than about, less than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. The average diameter of the droplets can be about 0.001 microns to about 0.01 microns, about 0.001 microns to about 0.005 microns, about 0.001 microns to about 0.1 microns, about 0.001 microns to about 1 micron, about 0.001 microns to about 10 microns, about 0.001 microns to about 100 microns, about 0.001 microns to about 500 microns, about 0.01 microns to about 0.1 microns, about 0.01 microns to about 1 micron, about 0.01 microns to about 10 microns, about 0.01 microns to about 100 microns, about 0.01 microns to about 500 microns, about 0.1 microns to about 1 micron, about 0.1 microns to about 10 microns, about 0.1 microns to about 100 microns, about 0.1 microns to about 500 microns, about 1 micron to about 10 microns, about 1 micron to about 100 microns, 1 micron to about 500 microns, about 10 microns to about 100 microns, about 10 microns to about 500 microns, or about 100 microns to about 500 microns.

Droplet volume can be about, more than about, less than about, or at least about 0.001 nL, 0.01 nL, 0.1 nL, 1 nL (100 μm$^3$), 10 nL, or 100 nL. Droplets can be generated using, e.g., RAINSTORM™ (RAINDANCE™), microfluidics from ADVACED LIQUID LOGIC, or ddPCR™ (BIO-RAD).

Microfluidic methods of producing emulsion droplets using microchannel cross-flow focusing or physical agitation can produce either monodisperse or polydisperse emulsions. The droplets can be monodisperse droplets. The droplets can be generated such that the size of said droplets does not vary by more than plus or minus 5% of the average size of said droplets. The droplets can be generated such that the size of said droplets does not vary by more than plus or minus 2% of the average size of said droplets. A droplet generator can generate a population of droplets from a single sample, wherein none of the droplets can vary in size by more than plus or minus 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Both the flow rate in a droplet generator and the length of nucleic acids in a sample can have an impact on droplet generation. One way to decrease extension is to decrease flow rate; however, this can have the undesirable side effect of lower throughput and also increased droplet size. Long nucleic acids can disrupt droplet formation in extreme cases, resulting in a steady flow rather than discrete droplets. Reducing nucleic acid size in a sample can improve droplet formation when nucleic acid loads are high. Samples with high nucleic acid loads (e.g., high DNA loads, high RNA loads, etc.) can be used. Reducing the length of nucleic acids in a sample (e.g., by digestion, sonication, heat treatment, or shearing) can improve droplet formation.

Higher mechanical stability can be useful for microfluidic manipulations and higher-shear fluidic processing (e.g., in microfluidic capillaries or through 90 degree turns, such as valves, in a fluidic path). Pre- and post-thermally treated droplets or capsules can be mechanically stable to standard pipette manipulations and centrifugation.

A droplet can be formed by flowing an oil phase through an aqueous sample. A partition, e.g., an aqueous phase of an emulsion, can comprise a buffered solution and reagents for performing an amplification reaction, e.g., a PCR reaction, including nucleotides, primers, probe(s) for fluorescent detection, template nucleic acids, DNA polymerase enzyme, and/or reverse transcriptase enzyme.

A partition, e.g., an aqueous phase of an emulsion, can comprise a buffered solution and reagents for performing an enzymatic reaction (e.g., a PCR) without solid-state beads, such as magnetic-beads. The buffered solution can comprise about, more than about, at least about, or less than about 1, 5, 10, 15, 20, 30, 50, 100, or 200 mM Tris. A partition, e.g., an aqueous phase of an emulsion, can comprise one or more buffers including, e.g., TAPS, bicine, Tris, Tricine, TAPSO, HEPES, TES, MOPS, PIPES, cacodylate, SSC, ADA, ACES, cholamine chloride, acetamidoglycine, glycinamide, maleate, phosphate, CABS, piperidine, glycine, citrate, glycylglycine, malate, formate, succinate, acetate, propionate, pyridine, piperazine, histidine, bis-tris, ethanolamine, carbonate, MOPSO, imidazole, BIS-TRIS propane, BES, MOBS, triethanolamine (TEA), HEPPSO, POPSO, hydrazine, Trizma (tris), EPPS, HEPPS, bicine, HEPBS, AMPSO, taurine (AES), borate, CHES, 2-amino-2-methyl-1-propanol (AMP), ammonium hydroxide, methylamine, or MES. The pH of the partition, e.g., an aqueous phase of an emulsion, can be about 2, 2.5, 3, 3.5, 4, 4.5, 5, 5.5, 6, 6.5, 6.6, 6.7, 6.8, 6.9, 7, 7.1, 7.2, 7.3, 7.4, 7.5, 7.5, 7.6, 7.7, 7.8, 7.9, 8, 8.1, 8.2, 8.3, 8.4, 8.5, 8.6, 8.7, 8.8, 8.9, 9, 9.5, 10, 10.5, 11, 11.5, 12, or 12.5. The pH of the partition, e.g., an aqueous phase of an emulsion, can be about 5 to about 9, about 5 to about 8, about 5 to about 7, about 6.5 to about 8, about 6.5 to about 7.5, about 6 to about 7, about 6 to about 9, or about 6 to about 8.

A partition, e.g., an aqueous phase of an emulsion, can comprise a salt, e.g., potassium acetate, potassium chloride, magnesium acetate, magnesium chloride, sodium acetate, or sodium chloride. The concentration of potassium chloride can be about, more than about, at least about, or less than about 10, 20, 30, 40, 50, 60, 80, 100, 200 mM. The buffered solution can comprise about 15 mM Tris and about 50 mM KCl.

A partition, e.g., an aqueous phase of an emulsion, can comprise nucleotides. The nucleotides can comprise deoxyribonucleotide triphosphate molecules, including dATP, dCTP, dGTP, dTTP, in concentrations of about, more than about, less than about, or at least about 50, 100, 200, 300, 400, 500, 600, or 700 µM each. dUTP can be added within a partition, e.g., an aqueous phase of an emulsion, to a concentration of about, less than about, more than about, or at least about 50, 100, 200, 300, 400, 500, 600, 700, 800, 900, or 1000 µM. The ratio of dUTP to dTTP in a partition, e.g., an aqueous phase of an emulsion, can be about 1:1000, 1:500, 1:250, 1:100, 1:75, 1:50, 1:40, 1:30, 1:20, 1:10, 1:5, 1:4, 1:3, 1:2, or 1:1.

A partition, e.g., an aqueous phase of an emulsion, can comprise one or more divalent cations. The one or more divalent cations can be, e.g., $Mg^{2+}$, $Mn^{2+}$, $Cu^{2+}$, $Co^{2+}$, or $Zn^{2+}$ Magnesium chloride ($MgCl_2$) can be added to a partition, e.g., an aqueous phase of an emulsion, at a concentration of about, more than about, at least about, or less than about 1.0, 2.0, 3.0, 4.0, or 5.0 mM. The concentration of $MgCl_2$ can be about 3.2 mM. Magnesium sulfate can be substituted for magnesium chloride, at similar concentrations. A partition, e.g., an aqueous phase of an emulsion, can comprise both magnesium chloride and magnesium sulfate. A wide range of common, commercial PCR buffers from varied vendors can be substituted for the buffered solution.

A non-ionic Ethylene Oxide/Propylene Oxide block copolymer can be added to a partition, e.g., an aqueous phase of an emulsion, in a concentration of about, more than about, less than about, or at least about 0.1%, 0.2%, 0.3%, 0.4%, 0.5%, 0.6%, 0.7%, 0.8%, 0.9%, or 1.0%. A partition, or aqueous phase, can comprise a biosurfactant. Common biosurfactants include non-ionic surfactants such as Pluronic F-68, Tetronics, Zonyl FSN. Pluronic F-68 can be present at a concentration of about 0.5% w/v.

Additives

A partition, e.g., an aqueous phase of an emulsion, can comprise one or more additives including, but not limited to, non-specific background/blocking nucleic acids (e.g., salmon sperm DNA), biopreservatives (e.g., sodium azide), PCR enhancers (e.g., betaine (N,N,N-trimethylglycine; [carboxymethyl]trimethylammonium), trehalose, etc.), and/or inhibitors (e.g., RNAse inhibitors). A GC-rich additive comprising, e.g., betaine and DMSO, can be added to samples assayed in the methods provided herein.

The one or more additives can include a non-specific blocking agent such as BSA or gelatin from bovine skin. The gelatin or BSA can be present in a concentration range of approximately 0.1 to about 0.9% w/v. Other blocking agents can include betalactoglobulin, casein, dry milk, or other common blocking agents. In some cases, the concentration of BSA and gelatin are about 0.1% w/v.

The one or more additives can include 2-pyrrolidone, acetamide, N-methylpyrolidone (NMP), B-hydroxyethylpyrrolidone (HEP), propionamide, NN-dimethylacetamide (DMA), N-methylformamide (MMP), NN-dimethylformamide (DMF), formamide, N-methylacetamide (MMA), polyethylene glycol, tetramethylammonium chloride (TMAC), 7-deaza-2'-deoxyguanosine, T4 gene 32 protein, glycerol, or nonionic detergent (Triton X-100, Tween 20, Nonidet P-40 (NP-40), Tween 40, SDS (e.g., about 0.1% SDS)), salmon sperm DNA, sodium azide, formamide, dithiothreitol (DTT), betamercaptoethanol (BME), 2-mercaptoethylamine-HCl, tris(2-carboxythyl)phosphine (TCEP), cysteine-HCl, or a plant polysaccharide. The one or more additives can be ethanol, ethylene glycol, dimethylacetamide, dimethylformamide, or suphalane.

Primers

A partition, e.g., an aqueous phase of an emulsion, can comprise oligonucleotide primers. The oligonucleotide primers can be used for amplification. Primers for amplification within a partition, e.g., an aqueous phase of an emulsion, can have a concentration of about, more than about, less than about, or at least about 0.1, 0.2, 0.3, 0.4, 0.5, 0.6, 0.7, 0.8, 0.9, or 1.0 µM. The concentration of each primer can be about 0.5 µM. Primers can be designed according to known parameters for avoiding secondary structures and self-hybridization. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers may be able to hybridize to the genetic targets described herein. About 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers can be used.

Primers can be prepared by a variety of methods including but not limited to cloning of appropriate sequences and direct chemical synthesis using methods well known in the art (Narang et al., *Methods Enzymol.* 68:90 (1979); Brown et al., *Methods Enzymol.* 68:109 (1979)). Primers can also be obtained from commercial sources such as Integrated DNA Technologies, Operon Technologies, Amersham Pharmacia Biotech, Sigma, or Life Technologies. The primers can have an identical melting temperature. The melting temperature of a primer can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. The melting temperature of a primer can be about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C.

The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer can be calculated using software programs such as Net Primer (free web based program at http://www.premierbiosoft.com/netprimer/index.html). The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest; thus the TM can be recalculated based on both the sequences of the 5' half and the 3' half of each primer.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest, thus the TM can be recalculated based on both the sequences of the 5' half and the 3' half of each primer.

Probes

A partition, e.g., an aqueous phase of an emulsion, can comprise one or more probes for fluorescent detection. The concentration of each of the one or more probes can be about, more than about, at least about, or less than about 0.1, 0.2, 0.3, 0.4, or 0.5 µM. The concentration of the one or more probes for fluorescent detection can be about 0.25 µM. Amenable ranges for target nucleic acid concentrations in PCR can be between about 1 pg and about 500 ng. A probe can be about, more than about, less than about, or at least about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases long. A probe can be about 8 to about 40, about 10 to about 40, about 10 to about 35, about 10 to about 30, about 10 to about 25, about 10 to about 20, about 15 to about 40, about 15 to about 35, about 15 to about 30, about 15 to about 25, about 15 to about 20, about 18 to about 40, about 18 to about 35, about 18 to about 30, about 18 to about 25, or about 18 to 22 bases. A label (fluorophore, dye) used on a probe (e.g., a Taqman probe) can be, e.g., 6-carboxyfluorescein (FAM), tetrachlorofluorescin (TET), 4,7,2'-trichloro-7'-phenyl-6-carboxyfluorescein (VIC), HEX, Cy3, Cy 3.5, Cy 5, Cy 5.5, Cy 7, tetramethylrhodamine, ROX, and JOE, Alexa Fluor dye, e.g., Alexa Fluor 350, 405, 430, 488, 532, 546, 555, 568, 594, 633, 647, 660, 680, 700, and 750; Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X. The label can be at the 5' end of a probe, 3' end of the probe, at both the 5' and 3' end of a probe, or internal to the probe. A unique label can be used to detect each different locus in an experiment. A probe, e.g., a Taqman probe, can comprise a quencher, e.g., a 3' quencher. The 3' quencher can be, e.g., TAMARA, DABCYL, BHQ-1, BHQ-2, or BHQ-3. In some cases, a quencher used in the methods provided herein is a black hole quencher (BHQ). In some cases, the quencher is a minor groove binder (MGB). In some cases, the quencher is a fluorescent quencher. In other cases, the quencher is a non-fluorescent quencher (NFQ).

Polymerases

A partition, e.g., an aqueous phase of an emulsion, can comprise a polymerase. The polymerase can be a DNA polymerase. The DNA polymerase can be, e.g., T4 DNA polymerase, DEEP VENT™ DNA polymerase, LONGAMP® Taq, PHUSION® High Fidelity DNA polymerase, LONGAMP® Hot Start Taq, Crimson LONGAMP® Taq, Taq DNA polymerase, Crimson Taq DNA polymerase, ONETAQ® DNA polymerase, QUICK-LOAD® DNA polymerase, VENTR® DNA polymerase, Hemo KLENTAQ®, Bsu DNA polymerase, DNA polymerase I, DNA Polymerase I, Large (Klenow), Klenow Fragment, Phi29 DNA polymerase, Pfu DNA polymerase, Pfx DNA polymerase, Tth DNA polymerase, Vent DNA polymerase, bacteriophase 29, REDTAQ™, or T7 DNA polymerase. The DNA polymerase can comprise 3' to 5' exonuclease activity. The DNA polymerase can comprise 5' to 3' exonuclease activity. The DNA polymerase can comprise both 3' to 5' exonuclease activity and 5' to 3' exonuclease activity. The DNA polymerase can comprise neither 3' to 5' exonuclease activity nor 5' to 3' exonuclease activity. The DNA polymerase can comprise strand displacement activity. In some cases, the DNA polymerase does not comprise strand displacement activity. The error rate of the DNA polymerase can be less than $1 \times 10^{-6}$ bases.

A partition, e.g., an aqueous phase of an emulsion, can comprise a reverse transcriptase. The reverse transcriptase can be AMV reverse transcriptase or M-MuLV reverse transcriptase. The RNA polymerase can comprise 5' to 3' exonuclease activity. The reverse transcriptase can comprise both 3' to 5' exonuclease activity and 5' to 3' exonuclease activity. The reverse transcriptase can comprise neither 3' to 5' exonuclease activity nor 5' to 3' exonuclease activity. The reverse transcriptase can comprise strand displacement activity. In some embodiments, the reverse transcriptase does not comprise strand displacement activity.

A partition, e.g., an aqueous phase of an emulsion, can comprise an RNA polymerase. The RNA polymerase can be, e.g., phi6 RNA polymerase, SP6 RNA polymerase, or T7 RNA polymerase.

In some embodiments, a partition, e.g., an aqueous phase of an emulsion, comprises Poly(U) polymerase or Poly(A) polymerase.

Oil Phase

The oil phase can comprise a fluorinated base oil which can be additionally stabilized by combination with a fluorinated surfactant such as a perfluorinated polyether. The base oil can be one or more of HFE 7500, FC-40, FC-43, FC-70, or another common fluorinated oil. The anionic surfactant can be Ammonium Krytox (Krytox-AM), the ammonium salt of Krytox FSH, or morpholino derivative of Krytox-FSH. Krytox-AS can be present at a concentration of about, more than about, less than about, or at least about 0.1%, 0.2%, 0.3%, 0.4%, 0.5%, 0.6%, 0.7%, 0.8%, 0.9%, 1.0%, 2.0%, 3.0%, or 4.0% w/w. The concentration of Krytox-AS can be about 1.8%. The concentration of Krytox-AS can be about 1.62%. Morpholino derivative of Krytox-FSH can be present at a concentration of about, more than about, less than about, or at least about 0.1%, 0.2%, 0.3%, 0.4%, 0.5%, 0.6%, 0.7%, 0.8%, 0.9%, 1.0%, 2.0%, 3.0%, or 4.0% w/w. The concentration of morpholino derivative of Krytox-FSH can be about 1.8%. In some embodiments, the concentration of morpholino derivative of Krytox-FSH is about 1.62%.

The oil phase can comprise an additive for tuning the oil properties, such as vapor pressure or viscosity or surface tension. Nonlimiting examples include perfluoro-octanol and 1H, 1H,2H,2H-Perfluorodecanol. In some embodiments, 1H, 1H,2H,2H-Perfluorodecanol is added to a concentration of about 0.05%, 0.06%, 0.07%, 0.08%, 0.09%, 1.00%, 1.25%, 1.50%, 1.75%, 2.00%, 2.25%, 2.50%, 2.75%, or 3.00% w/w. In some embodiments, 1H,1H,2H, 2H-Perfluorodecanol is added to a concentration of 0.18% w/w.

Microcapsules

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about, more than about, or at least about 50, 60, 70, 80, 90, or 95 degrees Celsius. In some embodiments this heating occurs using a thermocycler. During the heating process, a fluid or mineral oil overlay can be used to prevent evaporation. Excess continuous phase oil may or may not be removed prior to heating. The biocompatible capsules can be resistant to coalescence and/or flocculation across a wide range of thermal and mechanical processing.

Following conversion, the capsules can be stored at about, more than about, less than about, or at least about 3, 4, 5, 6, 7, 8, 9, 10, 15, 20, 25, 30, 35, or 40 degrees Celsius, with one embodiment comprising storage of capsules at less than about 25 degrees Celsius. In some embodiments, these capsules are useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more nucleic acid probes (e.g., molecular inversion probe, ligation probe, etc.) and can resist coalescence, particularly at high temperatures. Accordingly, PCR amplification reactions can occur at a very high density (e.g., number of reactions per unit volume). In some embodiments, greater than 100,000, 500,000, 1,000,000, 1,500,000, 2,000,000, 2,500,000, 5,000,000, or 10,000,000 separate reactions can occur per ml. In some embodiments, the reactions occur in a single well, e.g., a well of a microtiter plate, without inter-mixing between reaction volumes. The microcapsules can also contain other components necessary to enable an enzymatic reaction (e.g., a PCR reaction) to occur, e.g., nucleotides, primers, probes, dNTPs, DNA or RNA polymerases, reverse transcriptases, restriction enzymes, etc. These capsules exhibit resistance to coalescence and flocculation across a wide range of thermal and mechanical processing.

The compositions described herein can include compositions comprising mixtures of two or more immiscible fluids such as oil and water that contain a type of nucleic acid probe (e.g., TaqMan probe, molecular inversion probe, ligation probe, etc.). In some cases, the composition comprises a restriction enzyme described herein, e.g., a droplet comprising a restriction enzyme (e.g., methylation-sensitive enzyme). In other embodiments, the compositions described herein comprise microcapsules that contain a type of nucleic acid (e.g., TaqMan probe, molecular inversion probe, ligation probe, etc.). Such microcapsules can resist coalescence, particularly at high temperatures, and therefore enable amplification reactions to occur at a very high density (e.g., number of reactions per unit volume).

Fragmentation

Library preparation within partitions (e.g., droplets) can entail fragmentation of polynucleotides in a sample and ligation of adaptors. Generally, the fragmentation occurs within a partition (e.g., droplet); but, in some applications, the fragmentation may occur prior to the partitioning. Fragmentation can be accomplished enzymatically, e.g., using an endonuclease. The endonuclease can be, e.g., AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrUU, BaeGI, BaeI, BamHI, BanI, BanII, BbsI, BbvCI, BbvI, Bed, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, Eco53kI, EcoNU, EcoO109I, EcoP15I, EcoRI, EcoRV, FatI, FauI, Fnu4HI, FokI, FseI, FspI, HaeII, HaeIII, HgaI, HhaI, HincII, HincIII, HinfI, HinP1I, HpaI, HpaII, HphI, Hpy166I, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NatI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AiwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfcI, SfoI, SgrAI, SmaI, SmlI, SnaBI, SpeI, SphI, SspI, StuI, StyD4I, StyO, SwaI, T, TaqαI, TfiI, TliI, TseI, Tsp45I, Tsp509I, TspMI, TspRI, Tth111I, XbaI, XcmI, XhoI, XmaI, XmnI, or ZraI In some embodiments, the fragmentation is mechanical fragmentation. In some embodiments, shear forces created during lysis or extraction can mechanically fragment polynucleotides. Fragmentation can be accomplished by, e.g, sonication, heat treatment, or shearing. In some embodiments, mechanical fragmentation is by nebulization.

In some embodiments, the endonuclease is a methylation sensitive restriction enzyme. In some embodiments, the methylation sensitive restriction enzyme specifically cleaves methylated polynucleotides. In some embodiments, the methylation sensitive restriction enzyme specifically cleaves unmethylated polynucleotides. A methylation sensitive enzyme can include, e.g., DpnI, Acc65I, KpnI, ApaI, Bsp120I, Bsp143I, MboI, BspOI, NheI, Cfr9I, SmaI, Csp6I, RsaI, Ecl136II, SacI, EcoRII, MvaI, HpaII, MSpJI, LpnPI, FsnEI, DpnII, McrBc, or MspI.

In some embodiments, fragmentation of a polynucleotide is accomplished by introducing one or more noncanonical nucleotides (e.g., dUTP) into a polynucleotide, generating one or more abasic sites by cleaving the base of the non-canonical nucleotide (e.g., using, e.g., Uracil N-Glycosylase (UNG) or Uracil DNA glycosylase (UDG)), and fragmenting the polynucleotide at the one or more abasic sites. The fragmenting can be by an enzymatic agent or a chemical agent. The chemical agent can be, e.g., a polyamine, e.g., N,N'-dimethylethylenediamine (DMED). The enzymatic agent can be, e.g., apurinic/apyrimidinic endonuclease (APE 1). In some embodiments, fragmentation can be accomplished as described in U.S. Patent Application Publication Nos. 20110033854 or 20100022403.

Ligation

Fragmentation can be followed by a step of ligating adaptors to polynucleotides. In some embodiments, a ligation step does not following a fragmentation step. A partition, e.g., an aqueous phase of an emulsion, can comprise a ligase. The ligase can be, e.g., T4 DNA ligase, *E. coli* DNA ligase, Taq DNA ligase, 9° N™ DNA ligase, T4 RNA ligase 1 (ssRNA ligase), T4 RNA ligase 2 (dsRNA ligase), or T4 RNA Ligase 2, truncated (NEB).

A partition, e.g., an aqueous phase of an emulsion, can comprise reagents for a ligation reaction, e.g., buffer, salt, and/or reducing agent. Ligase and other reagents can be supplied in a partition, e.g., an aqueous phase of an emulsion, separate from a partition, e.g., an aqueous phase of an emulsion, comprising polynucleotides. A partition, e.g., an aqueous phase of an emulsion, comprising ligase can be merged with a partition, e.g., an aqueous phase of an emulsion, comprising polynucleotides.

The ligation reaction can occur at a temperature of about, more than about, less than about, or at least about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99° C. The ligation can occur at about 4° C. to about 16° C., about 16° C. to about 25° C., about 25° C. to about 30° C., about 25° C. to about 37° C., about 37° C. to about 45° C., about 37° C. to about 50° C., or about 50° C. to about 65° C.

The ligation reaction can occur for a time period of about, more than about, less than about, or at least about 5 min, 15 min, 30 min, 45 min, or 60 min. The ligation reaction can occur for a time period of about, more than about, less than about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hr. The ligation reaction can last for about 5 min to about 15 min, about 5 min to about 30 min, about 5 min to about 45 min, about 5 min to about 60 min, about 30 min to about 60 min, about 30 min to about 90 min, about 30 min to about 120 min, about 1 hr to about 2 hr, about 1 hr to about 6 hr, about 1 hr to about 12 hr, about 12 hr to about 24 hr, or about 12 hr to about 48 hr.

A transposon-based approach such as that provided by NEXTERA™ can be used in which DNA is fragmented and an adaptor can be ligated in a single step reaction (see e.g., http://www.epibio.com/newsletter/16-3_4-6.pdf). A TRANSPOSOME™ complex can comprise free transposon ends and a transposase. A TRANSPOSOME™ complex can be incubated with target double strand DNA, and the target can be fragmented. The transferred strand of a transposon end oligonucleotide can be covalently attached to the 5' end of a target fragment. Transposon integration and strand transfer can occur via a staggered, dsDNA break within a target polynucleotide. The resulting fragments can have single-stranded gaps. The concentration of TRANSPOSOME™ complexes can be varied to control the size distribution of the fragmented and tagged DNA library. The transposon ends can comprise barcodes. Adaptor ligation can be followed with PCR amplification of ligated products to increase their concentrations.

The NEXTERA™ technology can be used to generate di-tagged libraries. The libraries can be optionally barcoded. The libraries can be compatible, e.g., with Roche/454 or ILLUMINA®/SOLEXA® sequencing platforms. To generate platform-specific libraries, free transposon ends or appended transposon ends can be used. Platform specific tags, and optional barcoding, can be introduced by, e.g., PCR. Amplification can occur by, e.g., emulsion PCR (emPCR) or bridge PCR (bPCR).

In some embodiments, the methods of ligating adaptors to polynucleotides are those described in U.S. Pat. No. 5,789,206 or Arneson et al. (2008) Whole-Genome Amplification by Adaptor-Ligation PCR of Randomly Sheared Genomic DNA (PRSG) Cold Spring Harbor Protocols.

Sizes of fragments of polynucleotides that can be generated can be about, more than about, at least about, or less than about 10, 25, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, or 10,000,000 bases or base pairs. In some embodiments, the size of fragmented polynucleotides is about 50 to about 100, about 50 to about 150, about 50 to about 200, about 100 to about 150, about 100 to about 200, about 100 to about 300, about 150 to about 200, about 150 to about 250, about 200 to about 300, about 200 to about 400, about 300 to about 400, about 300 to about 500, about 400 to about 500, about 400 to about 600, about 500 to about 600, about 500 to about 700, about 600 to about 700, about 600 to about 800, about 700 to about 800, about 700 to about 900, about 800 to about 1000, about 50 to about 500, about 100 to about 500, about 100 to about 1000, about 50 to about 1500, about 50 to about 2000, about 1000 to about 2000, or about 1500 to about 2000 bases or base pairs. In some embodiments, the size of fragmented polynucleotides is about 1000 to about 5000, about 1000 to about 10,000, about 10,000 to about 20,000, about 10,000 to about 50,000, about 10,000 to about 100,000, about 50,000 to about 100,000, about 100,000 to about 200,000, about 100,000 to about 500,000, about 100,000 to about 1,000,000, about 200,000 to about 1,000,000, about 300,000 to about 1,000,000, about 400,000 to about 1,000,000, about 500,000 to about 1,000,000, or about 750,000 to about 1,000,000 bases or base pairs.

Amplification

Polynucleotides may be amplified before they are partitioned. In some embodiments, polynucleotides are amplified while in a partition (e.g., aqueous phase of an emulsion, e.g., droplet). In some embodiments, polynucleotides are amplified before fragmentation in a partition. In some embodiments, polynucleotides are amplified after fragmentation in a partition. In some embodiments, polynucleotides are amplified both before and after fragmentation in a partition. In some embodiments, polynucleotides are amplified in a partition before ligating an adaptor to a polynucleotide in a partition. In some embodiments, polynucleotides are amplified in a partition after ligating an adaptor to the polynucleotide in the partition. In some embodiments, polynucleotides are amplified after ligating an adaptor to the polynucleotides and pooling polynucleotides from different partitions.

In some embodiments, the amplification comprises polymerase chain reaction (PCR), digital PCR, reverse-transcription PCR, quantitative PCR, real-time PCR, isothermal amplification, linear amplification, or isothermal linear amplification, quantitative fluorescent PCR (QF-PCR), multiplex fluorescent PCR (MF-PCR), single cell PCR, restriction fragment length polymorphism PCR(PCR-RFLP), PCR-RFLP/RT-PCR-RFLP, hot start PCR, nested PCR, in situ polony PCR, in situ rolling circle amplification (RCA), bridge PCR (bPCR), picotiter PCR, digital PCR, droplet digital PCR, or emulsion PCR (emPCR). Other suitable amplification methods include ligase chain reaction (LCR (oligonucleotide ligase amplification (OLA)), transcription amplification, cycling probe technology (CPT), molecular inversion probe (MIP)PCR, self-sustained sequence replication, selective amplification of target polynucleotide sequences, consensus sequence primed polymerase chain reaction (CP-PCR), arbitrarily primed polymerase chain reaction (AP-PCR), transcription mediated amplification (TMA), degenerate oligonucleotide-primed PCR (DOP-PCR), multiple-displacement amplification (MDA), strand displacement amplification (SDA), and nucleic acid based sequence amplification (NABSA). Other amplification methods that can be used herein include those described in U.S. Pat. Nos. 5,242,794; 5,494,810; 4,988,617; and 6,582,938.

In some embodiments, a multiple-displacement amplification (MDA) step can be performed within a partition (e.g., droplet) prior to fragmentation of polynucleotides and adaptor ligation to amplify the amount of DNA in each droplet in order to cover more of the captured polynucleotides. MDA can be a non-PCR based amplification technique that can involve annealing multiple primers (e.g., hexamer primers) to a polynucleotide template, and initiating DNA synthesis (e.g., using Phi 29 polymerase). When DNA synthesis proceeds to the next synthesis starting site, the polymerase can displace the newly produced DNA strand and continues its strand elongation. Strand displacement can generate newly synthesized single stranded DNA template to which other primers can anneal. Further primer annealing and strand displacement on the newly synthesized template can result in a hyper-branched DNA network. The sequence debranching during amplification can result in a high yield of products. To separate the DNA branching network, one or more S1 nucleases can be used to cleave the fragments at displacement sites. The nicks on the resulting DNA fragments can be repaired by DNA polymerase I. The generated DNA fragments can be directly used for analysis or be ligated to generate genomic libraries for further sequencing analysis. MDA is described, e.g., in U.S. Pat. No. 7,074,600.

Amplification of polynucleotides can occur on a bead. In other embodiments, amplification does not occur on a bead. A hot start PCR can be performed wherein the reaction is heated to 95° C. for two minutes prior to addition of the polymerase or the polymerase can be kept inactive until the first heating step in cycle 1. Hot start PCR can be used to minimize nonspecific amplification. Other strategies for and aspects of amplification suitable for use in the methods described herein are described in U.S. Patent Application Publication No. 2010/0173394 A1, published Jul. 8, 2010, which is incorporated herein by reference.

Any number of PCR cycles can be used to amplify the DNA, e.g., about, more than about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1 to about 45, about 10 to about 45, about 20 to about 45, about 30 to about 45, about 35 to about 45, about 10 to about 40, about 10 to about 30, about 10 to about 25, about 10 to about 20, about 10 to about 15, about 20 to about 35, about 25 to about 35, about 30 to about 35, or about 35 to about 40.

Thermocycling reactions can be performed on samples contained in droplets. The droplets can remain intact during thermocycling. Droplets can remain intact during thermocycling at densities of greater than about 10,000 droplets/mL, 100,000 droplets/mL, 200,000 droplets/mL, 300,000 droplets/mL, 400,000 droplets/mL, 500,000 droplets/mL, 600,000 droplets/mL, 700,000 droplets/mL, 800,000 droplets/mL, 900,000 droplets/mL or 1,000,000 droplets/mL. Droplets can remain intact during thermocycling at densities of greater than about 10,000 droplets/mL to about 100,000 droplets/mL, 10,000 droplets/mL to about 1,000,000 droplets/mL, or about 100,000 droplets/mL to about 1,000,000 droplets/mL. In other cases, two or more droplets may coalesce during thermocycling. In other cases, greater than about 100 or greater than about 1,000 droplets may coalesce during thermocycling.

Polynucleotides

The methods described herein can be used for manipulating and analyzing polynucleotides. The term polynucleotide, or grammatical equivalents, can refer to at least two nucleotides covalently linked together. A nucleic acid described herein can contain phosphodiester bonds, although in some cases, as outlined herein (for example in the construction of primers and probes such as label probes), nucleic acid analogs are included that can have alternate backbones, comprising, for example, phosphoramide (see e.g., Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470

(1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Chem. Soc.* 111:2321 (1989), O-methyl phosphoroamidate linkages (see e.g., Eckstein, Oligonucleotides and Analogues: A Practical Approach, Oxford University Press), and peptide nucleic acid (also referred to herein as "PNA") backbones and linkages (see e.g., Egholm, *J. Am. Chem. Soc.* 114:1895 (1992); Meier et al., *Chem. Int. Ed. Engl.* 31:1008 (1992); Nielsen, *Nature*, 365:566 (1993); Carlsson et al., *Nature* 380:207 (1996), all of which are incorporated by reference). Other analog nucleic acids include those with bicyclic structures including locked nucleic acids (LNAs are a class of nucleic acid analogues in which the ribose ring is "locked" by a methylene bridge connecting the 2'-O atom with the 4'-C atom), also referred to herein as "LNA" (see e.g., Koshkin et al., *J. Am. Chem. Soc.* 120.13252 3 (1998)); positive backbones (Denpcy et al., *Proc. Natl. Acad. Sci. USA* 92:6097 (1995); non-ionic backbones (see e.g., U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)), and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see e.g., Jenkins et al., *Chem. Soc. Rev.* (1995) pp 169-176). Several nucleic acid analogs are described in Rawls, *C & E News* Jun. 2, 1997 page 35. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid can contain any combination of deoxyribo- and ribo-nucleotides, and any combination of bases, including uracil, adenine, thymine, cytosine, guanine, inosine, xathanine hypoxathanine, isocytosine, isoguanine, etc.

The methods, compositions, and kits provided herein can be used to analyze polynucleotides (e.g., DNA, RNA, mitochondrial DNA, genomic DNA, mRNA, siRNA, miRNA, cRNA, single-stranded DNA, double-stranded DNA, single-stranded RNA, double-stranded RNA, tRNA, rRNA, cDNA, etc.). The methods, compositions and kits can be used to evaluate a quantity of a first polynucleotide compared to the quantity of a second polynucleotide. The methods can be used to analyze the quantity of synthetic plasmids in a solution; to detect a pathogenic organism (e.g., microbe, bacteria, virus, parasite, retrovirus, lentivirus, HIV-1, HIV-2, influenza virus, etc.) within a sample obtained from a subject or obtained from an environment. The methods also can be used in other applications wherein a rare population of polynucleotides exists within a larger population of polynucleotides. Polynucleotides can be obtained through cloning, e.g., cloning into plasmids, yeast, or bacterial artificial chromosomes. A polynucleotide can be obtained by reverse transcription of isolated mRNA.

In some embodiments, genomic DNA is analyzed. In some embodiments, the genomic DNA is from a mammal, e.g., a human. The genomic DNA can be obtained from normal somatic tissue, germinal tissue, or diseased tissue (e.g., tumor tissue). In some embodiments, about, more than about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 genome equivalents are used. A genome equivalent can be the amount of DNA in a single copy of a genome (e.g., a single diploid cell has 2 genome equivalents of DNA). In some embodiments, about 1 to about 10, about 1 to about 15, about 1 to about 20, about 1 to about 25, about 1 to about 30, about 1 to about 35, about 1 to about 40, about 1 to about 45, about 1 to about 50, about 1 to about 55, about 1 to about 60, about 5 to about 10, about 5 to about 15, about 5 to about 20, about 5 to about 25, about 5 to about 30, about 5 to about 35, about 5 to about 40, about 5 to about 45, about 5 to about 50, about 5 to about 55, about 5 to about 60, about 10 to about 20, about 10 to about 30, about 10 to about 40, about 10 to about 50, or about 10 to about 50 genome equivalents are used. In some embodiments, about, more than about, at least about, or less than about 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500, 000, 600,000, 700,000, 800,000, 900,000, 1,000,000, 2,000, 000, 3,000,000, 4,000,000, 5,000,000, 6,000,000, 7,000,000, 8,000,000, 9,000,000, or 10,000,000 genome equivalents are used. In some embodiments, about 100 to about 1000, about 100 to about 10,000, about 100 to about 100,000, about 100 to about 1,000,000, about 100 to about 10,000,000, about 1000 to about 10,000, about 1000 to about 100,000, about 1000 to about 1,000,000, about 1000 to about 10,000,000, about 10,000 to about 100,000, about 10,000 to about 1,000,000, about 10,000 to about 10,000,000, about 100,000 to about 1,000,000, about 100,000 to about 10,000,000, or about 1,000,000 to about 10,000,000 genome equivalents are used.

In some embodiments, polynucleotides are protected from shearing. Additives that can protect polynucleotides from shearing include, e.g., spermidine, spermine, poly(N-vinylpyrrolidone) 40 (PVP40), or $Co(NH_3)_6Cl_3$. In some embodiments, wide pore pipettes are used to avoid shearing of polynucleotides, e.g., when polynucleotides are transferred from one receptacle to another. Methods and compositions for protecting polynucleotides from shearing are described, e.g., in Kovacic et al. (1995) *Nucleic Acids Research* 23: 3999-4000 and Gurrieri S and Bustamante C. (1997) *Biochem J.* 326: 131-138.

The length of polynucleotides, or fragments of polynucleotides, that can be partitioned (e.g., in droplets) as described herein can be about, more than about, at least about, or less than about 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500, 000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, 100,000,000, 110,000,000, 120,000,000, 130,000,000, 140,000,000, 150,000,000, 160,000,000, 170,000,000, 180,000,000, 190,000,000, 200,000,000, 210,000,000, 220,000,000, 230,000,000, 240,000,000, or 250,000,000 nucleotides or base pairs in length.

Individual chromosomes can be separated into individual partitions. Human chromosomes that can be partitioned as described herein can include chromosomes 1, 2, 3, 4, 5, 6, 7, 8, 9, 10, 11, 12, 13, 14, 15, 16, 17, 18, 19, 20, 21, 22, X or Y.

In some embodiments, gentle processing steps are used to obtain large polynucleotides from a sample. The gentle processing steps can include, e.g., low speed centrifugation, release of genomic DNA using proteinase K and/or RNase digestion, or dialysis. In some embodiments, steps such as vortexing, high speed centrifugation, or ethanol precipitation are not performed.

Next Generation Sequencing

The methods, compositions, and kits described herein can be used with next generation sequence platforms. For example, adaptors with barcodes can be ligated to polynucleotides, different samples of polynucleotides with different barcodes can be pooled, the pooled polynucleotides can be sequenced using next generation sequencing, and barcodes can be used to determine which sequence reads are generated from polynucleotides in the same partition (e.g., droplet).

In some embodiments, the next generation sequencing technique is 454 sequencing (Roche) (see e.g., Margulies, M et al. (2005) *Nature* 437: 376-380). 454 sequencing can involve two steps. In the first step, DNA can be sheared into fragments of approximately 300-800 base pairs, and the fragments can be blunt ended. Oligonucleotide adaptors can then ligated to the ends of the fragments. The adaptors can serve as sites for hybridizing primers for amplification and sequencing of the fragments. The fragments can be attached to DNA capture beads, e.g., streptavidin-coated beads using, e.g., Adaptor B, which can contain 5'-biotin tag. The fragments can be attached to DNA capture beads through hybridization. A single fragment can be captured per bead. The fragments attached to the beads can be PCR amplified within droplets of an oil-water emulsion. The result can be multiple copies of clonally amplified DNA fragments on each bead. The emulsion can be broken while the amplified fragments remain bound to their specific beads. In a second step, the beads can be captured in wells (pico-liter sized; PicoTiterPlate (PTP) device). The surface can be designed so that only one bead fits per well. The PTP device can be loaded into an instrument for sequencing. Pyrosequencing can be performed on each DNA fragment in parallel. Addition of one or more nucleotides can generate a light signal that can be recorded by a CCD camera in a sequencing instrument. The signal strength can be proportional to the number of nucleotides incorporated. Pyrosequencing can make use of pyrophosphate (PPi) which can be released upon nucleotide addition. PPi can be converted to ATP by ATP sulfurylase in the presence of adenosine 5' phosphosulfate. Luciferase can use ATP to convert luciferin to oxyluciferin, and this reaction can generate light that is detected and analyzed.

In some embodiments, the next generation sequencing technique is SOLiD technology (Applied Biosystems; Life Technologies). In SOLiD sequencing, genomic DNA can be sheared into fragments, and adaptors can be attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations can be prepared in microreactors containing beads, primers, template, and PCR components. Following PCR, the templates can be denatured and beads can be enriched to separate the beads with extended templates. Templates on the selected beads can be subjected to a 3' modification that permits bonding to a glass slide. A sequencing primer can bind to adaptor sequence. A set of four fluorescently labeled di-base probes can compete for ligation to the sequencing primer. Specificity of the di-base probe can be achieved by interrogating every first and second base in each ligation reaction. The sequence of a template can be determined by sequential hybridization and ligation of partially random oligonucleotides with a determined base (or pair of bases) that can be identified by a specific fluorophore. After a color is recorded, the ligated oligonucleotide can be cleaved and removed and the process can be then repeated. Following a series of ligation cycles, the extension product can be removed and the template can be reset with a primer complementary to the n−1 position for a second round of ligation cycles. Five rounds of primer reset can be completed for each sequence tag. Through the primer reset process, most of the bases can be interrogated in two independent ligation reactions by two different primers. Up to 99.99% accuracy can be achieved by sequencing with an additional primer using a multi-base encoding scheme.

In some embodiments, the next generation sequencing technique is SOLEXA sequencing (Illumina sequencing). SOLEXA sequencing can be based on the amplification of DNA on a solid surface using fold-back PCR and anchored primers. SOLEXA sequencing can involve a library preparation step. Genomic DNA can be fragmented, and sheared ends can be repaired and adenylated. Adaptors can be added to the 5' and 3' ends of the fragments. The fragments can be size selected and purified. SOLEXA sequence can comprise a cluster generation step. DNA fragments can be attached to the surface of flow cell channels by hybridizing to a lawn of oligonucleotides attached to the surface of the flow cell channel. The fragments can be extended and clonally amplified through bridge amplification to generate unique clusters. The fragments become double stranded, and the double stranded molecules can be denatured. Multiple cycles of the solid-phase amplification followed by denaturation can create several million clusters of approximately 1,000 copies of single-stranded DNA molecules of the same template in each channel of the flow cell. Reverse strands can be cleaved and washed away. Ends can be blocked, and primers can by hybridized to DNA templates. SOLEXA sequencing can comprise a sequencing step. Hundreds of millions of clusters can be sequenced simultaneously. Primers, DNA polymerase and four fluorophore-labeled, reversibly terminating nucleotides can be used to perform sequential sequencing. All four bases can compete with each other for the template. After nucleotide incorporation, a laser is used to excite the fluorophores, and an image is captured and the identity of the first base is recorded. The 3' terminators and fluorophores from each incorporated base are removed and the incorporation, detection and identification steps are repeated. A single base can be read each cycle.

In some embodiments, the next generation sequencing technique comprises real-time (SMRT™) technology by Pacific Biosciences. In SMRT, each of four DNA bases can be attached to one of four different fluorescent dyes. These dyes can be phospholinked. A single DNA polymerase can be immobilized with a single molecule of template single stranded DNA at the bottom of a zero-mode waveguide (ZMW). A ZMW can be a confinement structure which enables observation of incorporation of a single nucleotide by DNA polymerase against the background of fluorescent nucleotides that can rapidly diffuse in an out of the ZMW (in microseconds). It can take several milliseconds to incorporate a nucleotide into a growing strand. During this time, the fluorescent label can be excited and produce a fluorescent signal, and the fluorescent tag can be cleaved off. The ZMW can be illuminated from below. Attenuated light from an excitation beam can penetrate the lower 20-30 nm of each ZMW. A microscope with a detection limit of 20 zeptoliters ($10^{-21}$ liters) can be created. The tiny detection volume can provide 1000-fold improvement in the reduction of background noise. Detection of the corresponding fluorescence of the dye can indicate which base was incorporated. The process can be repeated.

In some embodiments, the next generation sequencing is nanopore sequencing (See e.g., Soni G V and Meller A. (2007) *Clin Chem* 53: 1996-2001). A nanopore can be a small hole, of the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridION system. A single nanopore can be inserted in a polymer membrane across the top of a microwell. Each microwell can have an electrode for individual sensing. The microwells can be fabricated into an array chip, with 100,000 or more microwells per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., $SiN_x$, or $SiO_2$). The nanopore can be a hybrid pore (e.g., an integration of a protein pore into a solid-state membrane. The nanopore can be a nanopore with an integrated sensors (e.g., tunneling electrode detectors, capacitive detectors, or graphene based nano-gap or edge state detectors (see e.g., Garaj et al. (2010) *Nature* vol. 67, doi:10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some embodiments, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases. Nanopore sequencing technology from GENIA or NABsys can be used. In GENIA's technology, an engineered protein pore can be embedded in a lipid bilayer membrane, and "Active Control" technology can enable efficient nanopore-membrane assembly and control of DNA movement through the channel. In some embodiments, the next generation sequencing comprises ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can formed. Each well can hold a single DNA template. Beneath the well can be an ion sensitive layer, and beneath the ion sensitive layer can be an ion sensor. When a nucleotide is added to a DNA, H+ is released, when can be measured as a change in pH. The H+ ion can be converted to voltage and recorded by the semiconductor sensor. An array chip can be sequentially flooded with one nucleotide after another. No scanning, light, or cameras can be required.

In some embodiments, the next generation sequencing is DNA nanoball sequencing (as performed, e.g., by Complete Genomics; see e.g., Drmanac et al. (2010) *Science* 327: 78-81). DNA can be isolated, fragmented, and size selected. For example, DNA can be fragmented (e.g., by sonication) to a mean length of about 500 bp. Adaptors (Ad1) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a Type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adaptors bound can be PCR amplified (e.g., by PCR). Ad2 sequences can be modified to allow them to bind each other and form circular DNA. The DNA can be methylated, but a restriction enzyme recognition site can remain non-methylated on the left Ad1 adaptor. A restriction enzyme (e.g., AcuI) can be applied, and the DNA can be cleaved 13 bp to the left of the Ad1 to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template. Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamethyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

In some embodiments, the next generation sequencing technique is Helicos True Single Molecule Sequencing (tSMS) (see e.g., Harris T. D. et al. (2008) *Science* 320:106-109). In the tSMS technique, a DNA sample can be cleaved into strands of approximately 100 to 200 nucleotides, and a polyA sequence can be added to the 3' end of each DNA strand. Each strand can be labeled by the addition of a fluorescently labeled adenosine nucleotide. The DNA strands can then be hybridized to a flow cell, which can contain millions of oligo-T capture sites immobilized to the flow cell surface. The templates can be at a density of about 100 million templates/cm$^2$. The flow cell can then be loaded into an instrument, e.g., HELISCOPE™ sequencer, and a laser can illuminate the surface of the flow cell, revealing the position of each template. A CCD camera can map the position of the templates on the flow cell surface. The template fluorescent label can then be cleaved and washed away. The sequencing reaction can begin by introducing a DNA polymerase and a fluorescently labeled nucleotide. The oligo-T nucleic acid can serve as a primer. The DNA polymerase can incorporate the labeled nucleotides to the primer in a template directed manner. The DNA polymerase and unincorporated nucleotides can be removed. The templates that have directed incorporation of the fluorescently labeled nucleotide can be detected by imaging the flow cell surface. After imaging, a cleavage step can remove the fluorescent label, and the process can be repeated with other fluorescently labeled nucleotides until a desired read length is achieved. Sequence information can be collected with each nucleotide addition step. The sequencing can be asynchronous. The sequencing can comprise at least 1 billion bases per day or per hour.

In some embodiments, the sequencing technique can comprise paired-end sequencing in which both the forward and reverse template strand can be sequenced. In some embodiments, the sequencing technique can comprise mate pair library sequencing. In mate pair library sequencing, DNA can be fragments, and 2-5 kb fragments can be end-repaired (e.g., with biotin labeled dNTPs). The DNA fragments can be circularized, and non-circularized DNA can be removed by digestion. Circular DNA can be fragmented and purified (e.g., using the biotin labels). Purified fragments can be end-repaired and ligated to sequencing adaptors.

In some embodiments, a sequence read is about, more than about, less than about, or at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or 3000 bases. In some embodiments, a sequence read is about 10 to about 50 bases, about 10 to about 100 bases, about 10 to about 200 bases, about 10 to about 300 bases, about 10 to about 400 bases, about 10 to about 500 bases, about 10 to about 600 bases, about 10 to about 700 bases, about 10 to about 800 bases, about 10 to about 900 bases, about 10 to about 1000 bases, about 10 to about 1500 bases, about 10 to about 2000 bases, about 50 to about 100 bases, about 50 to about 150 bases, about 50 to about 200 bases, about 50 to about 500 bases, about 50 to about 1000 bases, about 100 to about 200 bases, about 100 to about 300 bases, about 100 to about 400 bases, about 100 to about 500 bases, about 100 to about 600 bases, about 100 to about 700 bases, about 100 to about 800 bases, about 100 to about 900 bases, or about 100 to about 1000 bases.

In some embodiments, the sequencing depth is about, more than about, at least about, or less than about 1×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×60×, 61×, 63×, 64×, 65×, 66×, 67×, 68×, 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, 100×, 110×, 120×, 130×, 140×, 150×, 160×, 170×, 180×, 190×, 200×, 210×, 220×, 230×, 240×, 250×, 260×, 270×, 280×, 290×, 300×, 350×, 400×, 450×, 500×, 550×, 600×, 650×, 700×, 750×, 800×, 850×, 900×, 950×, 1000×, 2000×, 3000×, 4000×, 5000×, 6000×, 7000×, 8000×, 9000×, 10,000×. In some embodiments, the sequencing depth is about 1× to about 4×, about 1× to about 5×, about 1× to about 8×, about 1× to about 10×, about 2× to about 4×, about 2× to about 8×, about 2× to about 10×, about 5× to about 10×, about 3× to about 6×, about 10× to about 15×, about 10× to about 20×, about 15× to about 20×, about 15× to about 25×, about 15× to about 30×, about 20× to about 30×, about 25× to about 30×, about 25× to about 50×, about 25× to about 75×, about 25× to about 100×, about 50× to about 100×, about 100× to about 200×, about 100× to about 500×, about 100× to about 1000×, about 200× to about 500×, about 500× to about 750×, about 500× to about 1000×, about 750× to about 1000×, about 1000× to about 2000×, about 1000× to about 5000×, about 1000× to about 10,000×, about 2000× to about 5000×, or about 5000× to about 10,000×. Depth of sequencing can be the number of times a sequence (e.g., a genome) is sequenced. In some embodiments, the Lander/Waterman equation is used for computing coverage. The general equation can be: C=LN/G, where C=coverage; G=haploid genome length; L=read length; and N=number of reads.

Applications

Long Reads, Phasing and De Novo Sequencing

In some embodiments, the methods, compositions, and kits described herein can be used for haplotype phasing. In some embodiments, short read sequencers, such as those made by Illumina and ABI, can be unable to provide phasing information. These sequencers can produce reads of 100-200 bases and as short as 30 bases. 454 sequencing (Roche) can produce sequence reads of about 400 bases. In some embodiments, 400 bases can be too short to yield sufficient phasing information. Sequencing using technology from Pacific Biosciences can produce sequence reads of about 1000 bases. In some embodiments, 1000 bases is too short to provide phasing information.

Short sequence reads can make it challenging to sequence a large genome de-novo. Short sequence reads can make it difficult to determine phasing information for all but a very small fraction of polymorphisms. The partitioning and barcoding schemes described herein can be used to reconstruct longer reads using long range assembly and supply phasing information while making use of existing sequencing approaches.

Next generation sequencing platforms can entail a library preparation step. Genomic DNA can be fragmented, optionally sized, and ligated to nucleic acid sequence (e.g., an adaptor) that can provide hybridization sites for a common set of primers. A common set of primers can be used for massive clonal amplification, e.g., in solution or on a solid support. In some embodiments, these clones can then be sequenced because the presence of a massive amount of identical sequence in a tightly confined space can allow for the amplification of a fluorescent (or other) signal emitted by the sequencing reaction.

Tag sequences can be appended to regions that serve as binding sites for primers so that a common barcode can be ligated to every sequence from a particular sample. Libraries from different samples can be mixed and sequenced in a single run. Because every read can contain a barcode, it can be determined which sample produced any given sequence read. This process can be known as sample multiplexing and can allow for much more cost effective pricing per sample for many sequencing applications. In some embodiments, part of every sequence read includes barcode sequence.

In some embodiments, a high molecular weight DNA sample can be partitioned so that a given partition is unlikely to contain two fragments from the same locus but different chromosomes. In some embodiments, high molecular weight DNA can comprise polynucleotides of greater than about 10,000, 100,000, 1,000,000, 10,000,000, 100,000,000, or 200,000,000 bases or base pairs. In some embodiments, polynucleotides are separated such that it is a rare event to have any given region of a genome of both a maternal and paternal polynucleotide in the same partition. In some embodiments, less than 10%, 9%, 8%, 7%, 6%, 5%, 4%, 3%, 2%, 1%, 0.1%, 0.01%, or 0.001% of partitions have two fragments from the same locus but from different chromosomes. In some embodiments, a sample is partitioned such that about, or less than about 20%, 19%, 18%, 17%, 16%, 15%, 14%, 13%, 12%, 11%, 10%, 9%, 8%, 7%, 6%, 5%, 4%, 3%, 2%, 1%, 0.1%, 0.01%, or 0.001% of a haploid genome is found per partition (e.g., droplet). In some embodiments, a sample is partitioned such that about 0.1% to about 1%, about 0.5% to about 1%, about 0.25% to about 0.75%, about 1% to about 5%, about 1% to about 2%, about 1% to about 10%, or about 5% to about 10% of a haploid genome is found per partition (e.g., droplet).

Library preparation can be performed within partitions (e.g., droplets) as described herein. Sequence reads that map somewhat close to each other in a genome and are determined to be from the same partition (e.g., in the same droplet) are likely linked to each other and thus reside on the same chromosome. In this fashion individual, short reads can be strung together into longer sequence fragments. See e.g., Example 1.

Single Cell Analysis

In some embodiments, the methods and compositions described herein can be used to analyze cells, e.g., individual cells. For example, individual cells can be separated into unique partitions, uniquely barcoded adaptors can be added to each partition, polynucleotides, or fragments of polynucleotides, within each partition can be barcoded by ligating adaptors to the polynucleotides or fragments of polynucleotides, barcoded polynucleotides from each partition can be pooled, the pooled polynucleotides can be sequenced, and barcodes can be used to determine if sequence reads were generated in the same or different partitions, and thus, in the same or different cells. In some embodiments, the methods and compositions described herein are used for single cell transcriptome sequencing, single cell genomic sequencing, or single cell methylome sequencing.

There are approximately 210 different types of cells in the human body. The individual cells that are partitioned can be any type of cell in the human body. A cell can be, e.g., a hormone secreting cell, an exocrine secretory epithelial cell, a keratinizing epithelial cell, a wet stratified barrier epithelial cell, a sensory transducer cell, an autonomic neuron cell, a sense organ or peripheral neuron supporting cell, a central nervous system neuron or glial cell, a lens cell, a metabolism or storage cell, a kidney cell, an extracellular matrix cell, a contractile cell, a blood or immune system cell, a pigment cell, a germ cell, a nurse cell, or an interstitial cell. The blood or immune system cell can be, e.g., erythrocyte (red blood cell), megakaryocyte (platelet precursor), monocyte, connective tissue macrophage, epidermal Langerhans cell, osteoclast, dendritic cell, microglial cell, neutrophil granulocyte, eosinophil granulocyte, basophil granulocyte, mast cell, Helper T cell, Suppressor T cell, Cytotoxic T cell, Natural Killer T cell, B cell, Natural killer cell, reticulocyte, or stem cell.

Individual cells can be from other types of samples described herein.

In some embodiments, the individual cell is from an environmental sample. In some embodiments, an environmental sample is separated into a plurality of partitions. The environmental sample can be, e.g., air, water, agricultural, or soil. The environmental sample can be, e.g., from a creek, river, pond, lake, lagoon, run, delta, marsh, salt marsh, swamp, mangrove swamp, mill pond, moat, sea, barachois, basin, bayou, beck, boil, canal, cove, estuary, gulf, harbor, inlet, ocean, bay, sewage treatment facility, slough, sound, spring, stream, tide pool, wash, wetland, Superfund site, coal mine, farm, field, desert, glacier, mountain, or mere. In some embodiments, a sample is from a pool (e.g., swimming pool), gymnasium, school, workplace, office, lobby, elevator, restroom, hospital, medical office, ventilation shaft, or restaurant. In some embodiments, an environmental sample can be from a surface, e.g., floor, table, skin, keyboard, computer, laptop, crime screen evidence (e.g., a weapon, e.g., gun or knife), or doorknob. In some embodiments, the sample is from a bioterrorist attack. In some embodiments, the sample comprises bacteria and/or viruses. In some embodiments, the sample comprises about, at least about, more than about, or less than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, or 100,000 different species and/or types of viruses. In some embodiments, and environmental sample comprises about 10 to about 100, about 10 to about 1000, about 100 to about 1000, about 100 to about 10,000, about 1000 to 10,000, about 10,000 to about 50,000, or about 10,000 to about 100,000 different species and/or types of viruses.

Single Cell Transcriptome Sequencing

In one aspect, single cells can be captured within separate partitions (e.g., droplets), and the single cells can be lysed. Messenger RNA from the individual cells in each partition (e.g., droplet) can be reverse transcribed with partition-specific barcoded primers. In some embodiments, the appropriate reagents (e.g., reverse transcriptase, nucleotides) can be sequestered in a partition (e.g., droplet) that is inside a larger droplet. The inner droplet can be burst (e.g., by heating) when desired to allow the reverse transcriptase to contact the messenger RNA. A reverse transcription (RT) reaction can be followed by library prep, which can incorporate unique barcodes.

Calculations for the number of droplets and barcodes to be used in single cell transcriptome sequencing can be similar to those described in Example 1 for analyzing phasing. For example, for analyzing 2,000 cells, sufficient partitioning can be performed to capture each cell in a separate droplet. For example, the 2,000 cells can be partitioned among 20,000 partitions (e.g., droplets). Steps can be taken to ensure that each of the partitions (e.g., droplets) with cells receives a unique barcode (e.g., on adaptors). This goal can be accomplished, e.g., by using 10,000 different barcodes.

After partitioning, lysing, barcoding, and sequencing, sequence read data can be analyzed to determine which transcripts came from the same cell. In this way, the massive capacity of next generation sequencing can be applied to large collections of cells while preserving single cell resolution.

Single Cell Genomic Sequencing

In some instances, individual cells can be captured in separate partitions (e.g., droplets), and genomic DNA from a partition with a single cell can be uniquely barcoded (e.g., using adaptors). Barcoded genomic DNA from different partitions can be pooled and sequenced, and the barcodes can be used to determine which sequence reads are from the same cell. In some embodiments, genomic DNA is fragmented in a partition. In some embodiments, genomic DNA is amplified before and/or after adding adaptors with barcodes. In some embodiments, genomic DNA is not amplified before or after adaptors are ligated to the genomic DNA.

In some embodiments, the sequence coverage per cell can be shallow (e.g., few reads per locus). In some embodiments, single cell genomic DNA sequencing can be used to determine copy number variation (CNV).

In some embodiments, MDA is performed within a droplet on a cell's genome prior to fragmentation and adaptor ligation. In some embodiments, performing MDA can provide more genetic material from a cell to sequence. In some embodiments, MDA may introduce bias. In some embodiments, amplification may result in loss of some copy number variation (CNV) information. In some embodiments, MDA is not performed within a droplet on a cell's genome prior to fragmentation and adaptor ligation.

Single Cell Methylome Sequencing

In some embodiments, methods and compositions described herein can be used for analyzing genomic methylation. For example, methods described herein can be used for single cell methylome sequencing. In some embodiments, individual cells are partitioned, e.g., into droplets. The partitions can be comprised of methyl-sensitive enzymes (e.g., endonucleases). In some embodiments, the methyl-sensitive enzymes digest methylated sites. Each of the partitions can comprise uniquely barcoded adaptors. For example, partitions (e.g., droplets) comprising methyl-sensitive enzymes are merged with partitions comprising sample polynucleotides. The adaptors can be ligated to polynucleotides in the partition before or after digestion with the methyl-sensitive enzyme. Barcode tagged polynucleotides can be pooled, and the polynucleotides can be sequenced. Sequence reads from the same partition can be determined. Absence of sequence reads can indicate digestion of polynucleotides in a partition. In some embodiments, the methyl-sensitive enzymes do not digest methylated DNA, but digest unmethylated DNA.

Genomic Methylation

In some embodiments, methods and compositions described herein can be used for genomic methylation analysis. In some embodiments, polynucleotides can be treated with bisulfite. Bifsulfite can convert unmethylated cytosines to uracil. Bisulfite does not convert methylated cytosines to uracil. Treated and untreated polynucleotides can be partitioned into a plurality of partitions (e.g., droplets). Polynucleotides can be fragmented in the partitions. Uniquely barcoded adaptors can be provided to each partition and ligated to bisulfite treated polynucleotides. The tagged polynucleotides can be pooled and sequenced to determine the methylation status of nucleic acids from the same and different partitions.

Exosome Sequencing

Exosomes are generally organelles such as small extracellular vesicles that can contain RNA. Exosomes can contain mRNA and/or miRNA. In some embodiments, individual exosomes are partitioned into separate partitions (e.g., droplets). Exosomes can be partitioned such that on average, each partition comprises less than about five, four, three, two, or 1 exosomes. Reverse transcription can be used to convert RNA in the exosome into cDNA. Uniquely barcoded adaptors can be added to polynucleotides from a partitioned exosome. Polynucleotides from the partitions can be pooled, the pooled polynucleotides can be sequenced, and the barcodes can be used to determine which sequence reads were derived from the same exosome. Other types of organelles that can be analyzed can include mitochondria (e.g., mitochondrial DNA can be analyzed).

Metagenomics Sequencing

In another aspect, the methods and compositions described herein can be used for metagenomic analysis. Metagenomics can be the study of genetic material in an environmental sample. In some embodiments, individual viruses and/or bacteria in a sample, e.g., an environmental sample, can be partitioned into a plurality of partitions, adaptors with unique barcodes can be added to each partition, and individual organisms or viruses can have their genomes and/or transcriptomes sequenced. Sequence reads with the same barcode can be assembled to determine the sequence of genomes or transcriptomes of the organisms and/or viruses.

Microfluidics

In another aspect, a microfluidics device can be devised that can partition a sample comprising cells so that every cell ends up in a unique partition (e.g., chamber) with its own set of barcodes. The contents of each chamber can then be processed separately to dilute and further partition (e.g., through an emulsion) in order to enable whole genome or transcriptome amplification separately for each cell. Whole genome amplification or other amplification schemes can benefit from partitioning because of a reduction in competition between different parts of the genome or transcriptome.

Slugs

In another aspect, slugs can be made to capture individual cells and supply them with their own barcodes (e.g., by ligating adaptors with unique barcodes). Slugs can be serial slugs of reagent that completely fill the diameter of a flow tube. Those slugs can be broken into many (e.g., thousands or more) smaller droplets in order to perform unbiased whole genome/transcriptome amplification in droplets. In some embodiments, a slug can be broken down into about, at least about, more than about, or less than about 100, 200, 300, 400, 500, 600, 700, 800, 900, 1000, 2000, 3000, 4000, 5000, 6000, 7000, 8000, 9000, or 10,000 droplets. In some embodiments, a slug can be broken down into about 100 to about 500, about 100 to about 1000, about 500 to about 1000, about 1000 to about 1500, about 1000 to about 2000, about 1000 to about 5000, about 1000 to about 10,000, or about 5,000 to about 10,000 droplets. In some embodiments, whole genome amplification can work better in droplets than in bulk. The droplets from all the slugs can be mixed together because they are already furnished with adaptors with unique barcodes. Sequencing information can be used to determine which reads came from which slug.

Protein Expression and Nucleic Acid Information

In another embodiment, methods described herein can be used to capture cells with specific cell surface markers and analyze polynucleotides (e.g., DNA or RNA) from the cells. In some embodiments, antibodies can be linked to beads coated with short DNA fragments with a unique barcode. Each antibody can be associated with its own unique sequence. The antibodies could also be linked to droplets containing DNA fragments—which can be burst as appropriate. Cells can be pre-coated with these antibodies, then captured in larger droplets along with droplet/cell-specific barcode adaptors. Library prep can ensue as described herein, contents of the droplets can be sequenced, and it can be inferred which reads came from which cell by the barcodes. Thus, this technique allows one to, in addition to sequencing a cell's genome or transcriptome, obtain information about their proteins. In some embodiments, some of the same information can be captured via FACS.

An antibody can include polyclonal and monoclonal antibodies, as well as antigen binding fragments of such antibodies. An antibody, or antigen binding fragment of such an antibody, can be characterized by having specific binding activity for a polypeptide or a peptide portion thereof of at least about $1 \times 10^5$ $M^{-1}$. Fab, F(ab')$_2$, Fd, Fv, single chain Fv (scFv) fragments of an antibody and the like, which retain specific binding activity for a polypeptide, can be used. Specific binding activity of an antibody for a polypeptide can be readily determined by one skilled in the art, for example, by comparing the binding activity of an antibody to a particular polypeptide versus a control polypeptide that is not the particular polypeptide. Methods of preparing polyclonal or monoclonal antibodies are well known to those skilled in the art (see, for example, Harlow and Lane, Antibodies: A Laboratory Manual, Cold Spring Harbor Laboratory Press (1988)).

An antibody can include naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (Science 246:1275-1281 (1989)). These and other methods of making functional antibodies are well known to those skilled in the art (Winter and Harris, Immunol. Today 14:243-246 (1993); Ward et al., Nature 341:544-546 (1989); Harlow and Lane, supra, 1988); Hilyard et al., Protein Engineering: A practical approach (IRL Press 1992); Borrabeck, Antibody Engineering, 2d ed. (Oxford University Press 1995)).

Samples

Samples to be analyzed using the methods, compositions, and kits provided herein can be derived from a non-cellular entity comprising nucleic acid (e.g., a virus) or from a cell-based organism (e.g., member of archaea, bacteria, or eukarya domains). A sample can be obtained in some cases from a hospital, laboratory, clinical or medical laboratory. The sample can comprise nucleic acid, e.g., RNA or DNA. The sample can comprise cell-free nucleic acid. In some cases, the sample is obtained from a swab of a surface, such as a door or bench top.

The sample can from a subject, e.g., a plant, fungi, eubacteria, archaeabacteria, protest, or animal. The subject may be an organism, either a single-celled or multi-cellular organism. The subject may be cultured cells, which may be primary cells or cells from an established cell line, among others. The sample may be isolated initially from a multi-cellular organism in any suitable form. The animal can be a fish, e.g., a zebrafish. The animal can be a bird, e.g., a chicken. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. In some embodiments, the human can be an infant, child, teenager, adult, or elderly person. The female can be pregnant, can be suspected of being pregnant, or planning to become pregnant. In some embodiments, the sample is from a plant. In some embodiments, the samples comprises one or more viruses.

The sample can be from a subject (e.g., human subject) who is healthy. In some embodiments, the sample is taken from a subject (e.g., an expectant mother) at at least 4, 5, 6, 7, 8, 9, 10, 11, 12, 13, 14, 15, 16, 17, 18, 19, 20, 21, 22, 23, 24, 25, or 26 weeks of gestation. In some embodiments, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The sample can be from a subject who has a specific disease, disorder, or condition, or is suspected of having (or at risk of having) a specific disease, disorder or condition. For example, the sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chromic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient.

The sample can be from a subject who is known to have a genetic disease, disorder or condition. In some cases, the subject is known to be wild-type or mutant for a gene, or portion of a gene, e.g., CFTR, Factor VIII (F8 gene), beta globin, hemachromatosis, G6PD, neurofibromatosis, GAPDH, beta amyloid, or pyruvate kinase gene. In some cases, the status of the subject is either known or not known, and the subject is tested for the presence of a mutation or genetic variation of a gene, e.g., CFTR, Factor VIII (F8 gene), beta globin, hemachromatosis, G6PD, neurofibromatosis, GAPDH, beta amyloid, or pyruvate kinase gene.

In other embodiments, the sample is taken from a female patient of child-bearing age and, in some cases, the female patient is not pregnant or of unknown pregnancy status. In still other cases, the subject is a male patient, a male expectant father, or a male patient at risk of, diagnosed with, or having a specific genetic abnormality. In some cases, the female patient is known to be affected by, or is a carrier of, a genetic disease or genetic variation, or is at risk of, diagnosed with, or has a specific genetic abnormality. In some cases, the status of the female patient with respect to a genetic disease or genetic variation may not be known. In further embodiments, the sample is taken from any child or adult patient of known or unknown status with respect to copy number variation of a genetic sequence. In some cases, the child or adult patient is known to be affected by, or is a carrier of, a genetic disease or genetic variation.

The sample can be aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, perspiration, tears, vaginal secretion, vomit, feces, or urine. The sample can be obtained from a hospital, laboratory, clinical or medical laboratory. The sample can taken from a subject. The sample can comprise nucleic acid. The nucleic acid can be, e.g., mitochondrial DNA, genomic DNA, mRNA, siRNA, miRNA, cRNA, single-stranded DNA, double-stranded DNA, single-stranded RNA, double-stranded RNA, tRNA, rRNA, or cDNA. The sample can comprise cell-free nucleic acid. The sample can be a cell line, genomic DNA, cell-free plasma, formalin fixed paraffin embedded (FFPE) sample, or flash frozen sample. A formalin fixed paraffin embedded sample can be deparaffinized before nucleic acid is extracted. The sample can be from an organ, e.g., heart, skin, liver, lung, breast, stomach, pancreas, bladder, colon, gall bladder, brain, etc.

In some embodiments, the sample is an environmental sample, e.g., air, water, agricultural, or soil.

When the nucleic acid is RNA, the source of the RNA can be any source described herein. For example, the RNA can a cell-free mRNA, can be from a tissue biopsy, core biopsy, fine needle aspirate, flash frozen, or formalin-fixed paraffin embedded (FFPE) sample. The FFPE sample can be deparaffinized before the RNA is extracted. The extracted RNA can be heated to about, more than about, less than about, or at least about 30, 31, 32, 33, 34, 35, 36, 37 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99° C. before analysis. The extracted RNA can be heated to any of these temperatures for about, or at least about, 15 min, 30 min, 45 min, 60 min, 1.5 hr, 2 hr, 2.5 hr, 3 hr, 3.5 hr, 4 hr, 4.5 hr, 5 hr, 5.5 hr, 6 hr, 6.5 hr, 7 hr, 7.5 hr, 8 hr, 8.5 hr, 9 hr, 9.5 hr, or 10 hr.

RNA can be used for a variety of downstream applications. For example, the RNA can be converted to cDNA with a reverse transcriptase and the cDNA can optionally be subject to PCR, e.g., real-time PCR. The RNA or cDNA can be used in an isothermal amplification reaction, e.g., an isothermal linear amplification reaction. The RNA, resulting cDNA, or molecules amplified therefrom can be used in a microarray experiment, gene expression experiment, Northern analysis, Southern analysis, sequencing reaction, next generation sequencing reaction, etc. Specific RNA sequences can be analyzed, or RNA sequences can be globally analyzed.

Nucleic acids can be extracted from a sample by means available to one of ordinary skill in the art.

The sample may be processed to render it competent for amplification. Exemplary sample processing can include lysing cells of the sample to release nucleic acid, purifying the sample (e.g., to isolate nucleic acid from other sample components, which may inhibit amplification), diluting/ concentrating the sample, and/or combining the sample with reagents for amplification, such as a DNA/RNA polymerase (e.g., a heat-stable DNA polymerase for PCR amplification), dNTPs (e.g., dATP, dCTP, dGTP, and dTTP (and/or dUTP)), a primer set for each allele sequence or polymorphic locus to be amplified, probes (e.g., fluorescent probes, such as TAQMAN probes or molecular beacon probes, among others) capable of hybridizing specifically to each allele sequence to be amplified, $Mg^{2+}$, DMSO, BSA, a buffer, or any combination thereof, among others. In some examples, the sample may be combined with a restriction enzyme, uracil-DNA glycosylase (UNG), reverse transcriptase, or any other enzyme of nucleic acid processing.

Computers

A computer can be used to store and process the data. A computer-executable logic can be employed to perform such functions grouping sequence reads by barcode sequence. A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods described herein. Provided herein are systems comprising computer readable instructions for performing methods described herein. Provided herein are computer readable medium comprising instructions which, when executed by a computer, cause the computer to perform methods described herein.

Kits

Provided herein are kits for performing methods described herein. The kits can comprise one or more restriction enzymes, endonucleases, exonucleases, ligases, polymerases, RNA polymerases, DNA polymerases, reverse transcriptases, topoisomerases, kinases, phosphatases, buffers, salts, metal ions, reducing agents, BSA, spermine, spermidine, glycerol, oligonucleotides, primers, probes, or labels (e.g., fluorescent labels). The kits can comprises one or more sets of instructions.

Multiplexing to Align the Dynamic Range of Targets Whose Concentrations are Different and to Smooth Out Biological Variation of Reference Genes Also provided herein are methods for estimating copy number variation (CNV). Copy number variation of one or more target sequences can play a role in a number of diseases and disorders. One method to analyze copy number variation of a target sequence is through a digital analysis, such as digital PCR, or droplet digital PCR. However, digital analysis of copy number of a target sequence can underestimate the number of copies of a target nucleic acid sequence in a sample if multiple copies of the target nucleic acid sequence are on the same polynucleotide in a sample. For example, in a digital PCR assay that has multiple compartments (e.g., partitions, spatially isolated regions), nucleic acids in a sample can be partitioned such that each compartment receives on average about 0, 1, 2, or several target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid. The number of compartments that contain a polynucleotide can be enumerated. However, if two copies of a target nucleic acid sequence are on a single polynucleotide, a compartment containing that polynucleotide can be counted as having only one target sequence.

Methods of analyzing CNVs are disclosed, e.g., in U.S. patent application Ser. No. 13/385,277, filed Feb. 9, 2012.

For example, methods can be used for physically separating target nucleic acids sequences. Often, the methods can avoid underestimating copy numbers of a target sequence due to the presence of multiple copies of the target sequence on a single polynucleotide. In some embodiments, a first sample of polynucleotides is obtained; the first sample can be, e.g., a genomic DNA sample. The target nucleic acid sequences in the first sample can be physically separated (e.g., by contacting the first sample with one or more restriction enzymes). The first sample can be separated into a plurality of partitions. The number of partitions with the target sequence can be enumerated. The copy number of the target can then be estimated.

The target nucleic acids can be identical; or, in other cases, the target nucleic acids can be different. In some cases, the target nucleic acids are located within the same gene. In some cases, the target nucleic acids are each located in a different copy (identical or near identical copy) of a gene. In still other cases, the target sequences are located within introns, or in a region between genes. Sometimes, one target sequence is located in a gene; and the second target sequence is located outside of the gene. In some cases, a target sequence is located within an exon.

Different targets within a sample may often be present at different copy numbers. In such cases, the target that is present at a lower copy number level, may be probed with multiple probes, each recognizing a different locus or region with the target sequence. For example, target A may be present at copy number 3, while target B is present at copy number 1. In such cases, target B may be probed with 3 primer/probe pairs to increase the number of B-positive droplets, or to increase the signal from droplets that comprise target B. The probes may be directed to different regions within target B. Often, the probes that target target B are labeled with the same label; but, in some cases, different labels may be used. Thus, such methods enable alignment of the dynamic range of targets with different copy numbers. Target B can be a different target or may be a reference sample, as described further herein. Therefore, such methods can also enable alignment of the dynamic range of targets with reference samples.

In some cases, a genome comprises one target sequence. In some cases, a genome comprises two or more target sequences. When a genome comprises two or more target sequences, the target sequences can be about, or more than about 50%, 55%, 60%, 65%, 70%, 75%, 80%, 85%, 90%, 95%, or 100% identical.

Separating two target sequences can comprise separating the target sequences by cleaving a specific site on the nucleic acid sequence. In some cases, the separating target nucleic acid sequences can comprise contacting the first sample with one or more restriction enzymes. Separating the target nucleic acid sequences can comprise digesting a polynucleotide at a site located between the target nucleic acid sequences. In some cases, the target nucleic acid sequences are each located within a gene. In some cases, the site that is targeted for digestion is located between the two genes. In some cases, the site selected for digestion is located in a gene; and, in some cases, the gene is the same gene as the gene which contains the target sequences. In other cases, the site selected for digestion is located in a different gene from that of the target sequence. In some cases, a target sequence and the site targeted for digestion are located in the same gene; and the target sequence is located upstream of the site targeted for digestion. In other cases, a target sequence and the site targeted for digestion are located in the same gene; but the target sequence is located downstream of the site targeted for digestion. In some cases, target nucleic acids can be separated by treatment of a nucleic acid sample with one or more restriction enzymes. In some cases, target nucleic acids can be separated by shearing. In some cases, target nucleic acids can be separated by sonication.

Following the separation step (e.g., digesting with one or more restriction enzymes), the sample can be partitioned into multiple partitions. Each of the plurality of partitions can comprise about 0, 1, 2 or several target polynucleotides. In some cases, each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 droplets have zero copies of a target nucleic acid.

Often, target nucleic acid is amplified in the partitions. In some cases, the amplification comprises use of one or more TaqMan probes.

In another embodiment, the method further comprises the step of enumerating the number of partitions comprising a reference nucleic acid sequence. A reference nucleic acid sequence can be known to be present in a certain number of copies per genome and can be used to estimate the number of genome copies of a target nucleic acid sequence in a sample. Estimating the copy number can comprise comparing the number of partitions comprising the target sequence to the number of partitions comprising the reference nucleic acid sequence. In another instance, a CNV estimate is determined by a ratio of the concentration of target nucleic acid sequence to a reference sequence.

In another embodiment, the method further comprises the step of analyzing a second sample, wherein the second sample and the first sample are derived from the same sample (e.g., a nucleic acid sample is split to the first sample and the second sample). The method can further comprise not contacting the second sample with one or more restriction enzymes. In some cases, the method further comprises separating the second sample into a plurality of partitions. The method can further comprise enumerating the number of partitions of the second sample that comprise the target sequence. In another embodiment, the method further comprises enumerating the number of partitions of the second sample that comprise a reference sequence. In another embodiment, the method comprises estimating the copy number of the target sequence in the second sample. In another embodiment, estimating the copy number of the target sequence in the second sample comprises comparing the number of partitions from the second sample with the target sequence and the number of partitions from the second sample with the reference sequence.

The copy number of the target sequence from the first sample and the copy number of the target sequence in the second sample can be compared to determine whether the copy number of the target sequence in the second sample was underestimated. The degree to which the copy number was underestimated may be indicative of whether interrogated copies were all on one chromosome or if at least one copy was on one homologous chromosome and at least one copy was on the other homologous chromosome. Values closer to one per diploid genome may indicate the first case, while values closer to two may indicate the second case.

Additional methods of determining copy number differences by amplification are described, e.g., in U.S. Patent Application Publication No. 20100203538. Methods for determining copy number variation are described in U.S. Pat. No. 6,180,349 and Taylor et al. (2008) *PLoS One* 3(9): e3179.

Copy number variations described herein can involve the loss or gain of nucleic acid sequence. Copy number variations can be inherited or can be caused by a de novo mutation. A CNV can be in one or more different classes. See, e.g. Redon et al. (2006) Global variation in copy number in the human genome. *Nature* 444 pp. 444-454. A CNV can result from a simple de novo deletion, from a simple de novo duplication, or from both a deletion and duplication. A CNV can result from combinations of multi-allelic variants. A CNV can be a complex CNV with de novo gain. A CNV can include about, or more than about 0, 1, 2, 3, 4, 5, 6, 7, 8, 9, or 10 contiguous genes. A CNV can include about 1 to about 10, about 1 to about 5, about 1 to about 4, about 1 to about 3, about 1 to about 2, about 0 to about 10, about 0 to about 5, or about 0 to about 2 contiguous genes. A copy number variation can involve a gain or a loss of about, or more than about, 100, 500, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 500,000, 750,000, 1 million, 5 million, or 10 million base pairs. In some cases, a copy number variation can involve the gain or loss of about 1,000 to about 10,000,000, about 10,000 to about 10,000,000, about 100,000 to about 10,000,000, about 1,000 to about 100,000, or about 1,000 to about 10,000 base-pairs of nucleic acid sequence. A copy number variation can be a deletion, insertion, or duplication of a nucleic acid sequence. In some cases, a copy number variation can be a tandem duplication.

In another embodiment, CNV haplotypes can be estimated from fluorescent signals generated by real-time PCR or ddPCR of partitioned samples. Before the late stages of a real-time PCR or ddPCR experiment, when reagents can become limiting, a partition with a higher copy number of a target sequence can have a higher signal than a partition with a lower copy number of the target sequence. In one embodiment, a sample (e.g., a subsample of a sample used in a linkage experiment) can be partitioned, and PCR can be performed on the partitions (e.g., droplets). The mean fluorescence intensity of partitions can be determined as they undergo exponential amplification for a target and/or reference nucleic acid sequence. The mean intensity can correspond to the number of starting copies of the target. If multiple targets are linked along a single polynucleotide strand, the intensity in the partition (e.g., droplet) that captures this strand may be higher than that of a partition (e.g., droplet) that captures a strand with only a single copy of the target. Excess presence of positive droplets with higher mean amplitudes can suggest the presence of a haplotype with multiple CNV copies. Conversely, presence of positive droplets with only low mean amplitudes can suggest that only haplotypes with single CNV copies are present in the sample. In another embodiment, the number of cycles used to estimate CNV can be optimized based on the size of the partitions and the amount of reagent in the partitions. For example, smaller partitions with lower amounts of reagent may require fewer amplification cycles than larger partitions that would be expected to have higher amounts of reagent.

The method can be useful because it can be used to analyze even target copies that are near each other on the polynucleotide, e.g., less than about 10, 9, 8, 7, 6, 5, 4, 5, 2, 1, 0.7 0.5, 0.3, 0.2, 0.1, 0.05, or 0.01 megabases apart; or that are very near each other on the polynucleotide, e.g., less than about 10, 9, 8, 7, 6, 5, 4, 3, 2, or 1 kilobase apart. In some cases, the method is useful for analyzing target copies that are very close to each other on the polynucleotide, e.g., within about 1, 10, 20, 30, 40, 50, 60, 70, 80, 90, 100, 200, 300, 400, 500, 600, 700, 800, 900, or 950 base pairs (bp's) apart. In some cases, the method is useful for analyzing target copies that are separated by zero (0) base pairs. In some cases, the method can be applied to identical, near identical, and completely different targets.

In some embodiments, the copy number of a target in a genome is about, more than about, less than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1000, 2000, 3000, 4000, 5000, 6000, 7000, 8000, 9000, 10,000, 20,000, 30,000, 40,000, 50,000, 60,000, 70,000, 80,000, 90,000, or 100,000 copies per haploid or diploid genome. In some embodiments, the copy number of a target is about 2 to about 5, about 2 to about 10, about 2 to about 20, about 2 to about 30, about 2 to about 40, about 2 to about 50, about 2 to about 100, about 5 to about 10, about 5 to about 25, about 5 to about 50, about 5 to about 100, about 10 to about 20, about 10 to about 50, about 10 to about 100, about 25 to about 50, about 25 to about 75, about 25 to about 100, about 100 to about 200, about 100 to about 500, about 100 to about 1000, about 500 to about 1000, about 1000 to about 5000, about 1000 to about 10,000, about 10,000 to about 20,000, about 10,000 to about 50,000, about 10,000 to about 100,000, or about 50,000 to about 100,000 per haploid or diploid genome.

In some embodiments, CNVs can be analyzed by measuring amounts of a target and a reference in a single reaction using probes with one fluorescence dye for the target and another for the reference. In some embodiments, e.g., when the target copy number is high, the concentration (or amount) of the target can be higher than the concentration (or amount) of the reference. In that case, it can be challenging to measure both the target and the reference in a single digital reaction (e.g., digital PCR), because the dynamic range of digital PCR can be limited. For example, a target may be present at 10,000 copies in a genome, but a reference may be present at only two copies per genome.

Figure 2:
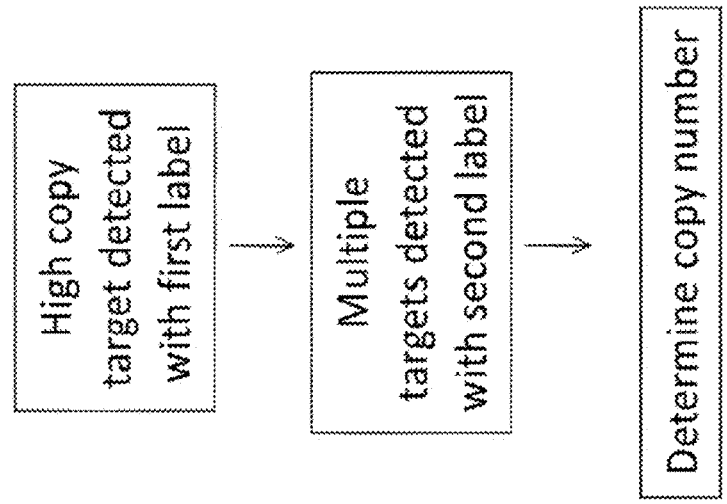
FIG. 2 illustrates a method of determining copy number of a high copy number target using references detected with a common label.

In some embodiments, several different targets for the reference can be multiplexed with each being detectable using probes with the same fluorescent dye. (See e.g., FIG. 2) Often, these different reference targets represent different regions or loci within the same reference polynucleotide (e.g., gene); although, in some cases, different reference polynucleotides (e.g., genes) can be used. Use of multiple references can boost the counts of the reference and bring them closer to the counts of the target. In some embodiments, about, more than about, at least about, or less than about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1000, 2000, 3000, 4000, 5000, 6000, 7000, 8000, 9000, 10,000, 20,000, 30,000, 40,000, 50,000, 60,000, 70,000, 80,000, 90,000, or 100,000 different references are used. In some embodiments, about 2 to about 5, about 2 to about 10, about 2 to about 20, about 2 to about 30, about 2 to about 40, about 2 to about 50, about 2 to about 100, about 5 to about 10, about 5 to about 25, about 5 to about 50, about 5 to about 100, about 10 to about 20, about 10 to about 50, about 10 to about 100, about 25 to about 50, about 25 to about 75, about 25 to about 100, about 100 to about 200, about 100 to about 500, about 100 to about 1000, about 500 to about 1000, about 1000 to about 5000, about 1000 to about 10,000, about 10,000 to about 20,000, about 10,000 to about 50,000, about 10,000 to about 100,000, or about 50,000 to about 100,000 different references are used. The reference can be any reference sequence described herein. Generally, the reference may be present at a different copy number than the target sequence. For example, the target may have copy number that is about, more than about, less than about, or at least about 1.5-fold, 2-fold, 2.5-fold, 3-fold, 3.5-fold, 4-fold, 4.5 fold, 5-fold, 6-fold, 7-fold, 8-fold, 9-fold, 10-fold, 20-fold, 50-fold, 75-fold, 100-fold, 200-fold, 500-fold, 700-fold, the copy number of the reference number. In other cases the copy number of the target is equal to that of the reference. In still other cases, the reference has a copy number that is about, more than about, less than about, or at least about 1.5-fold, 2-fold, 2.5-fold, 3-fold, 3.5-fold, 4-fold, 4.5 fold, 5-fold, 6-fold, 7-fold, 8-fold, 9-fold, 10-fold, 20-fold, 50-fold, 75-fold, or 100-fold the copy number of the target sequence.

In some embodiments, probes that anneal to each of the references can comprise the same label, e.g., fluorescent dye. Depending on the number of targets to be multiplexed, one can use universal probes, LNA probes, or ligation approaches. Any type of probe described herein can be used to multiplex references.

The methods described herein can be used to measure several gene expression targets in a single reaction. Several assays can be designed to target the lowest expressed gene and bring the measured counts closer to those of the higher expressed gene(s).

If the abundance of expression of two or more different targets on the same gene is being investigated, e.g., by converting mRNA to cDNA, a restriction digest on the cDNA can be performed in order to ensure that the different targets on a given gene end up in different partitions (e.g., droplets). Other methods of fragmenting nucleic acids described herein can be used to separate the targets.

The methods described herein can also apply to measuring viral load levels in a single reaction. A viral load can be measured by estimating the amount of virus in a bodily fluid. In some embodiments, determination of viral load can comprise PCR, reverse transcription PCR, or Nucleic Acid Sequence Based Amplification (NASBA) (transcription-based amplification system (TAS)). For example, PCR can be used to quantify integrated DNA (e.g., integrated into a chromosome of a cell). Reverse transcription PCR can be used to quantify viral RNA by converting it to cDNA. In some embodiments, NASBA is used to convert viral RNA into DNA, and the DNA can be transcribed into RNA. NASBA can involve annealing a primer to the 3' end of an RNA template, reverse transcribing the RNA template, degrading the RNA template with RNAse H, annealing a primer to the 5' end of the DNA strand, and using T7 RNA polymerase to produce a complementary RNA strand. The complementary RNA strand can be reused in the reaction cycle. In some embodiments, multiple references are used to such that the amount of viral nucleic acid and reference nucleic acid in a sample are within the dynamic range of the method used to determine the viral load. In some embodiments, probes used to detect the different references use the same label. In some embodiments, probes used to detect the references comprise different labels.

In some embodiments, multiplexing can also be useful for evening out biological variation where a reference varies in copy number from individual to individual. By averaging across multiple targets and/or reference sequences, the impact of the variation can be reduced. This method can be used, e.g., for diagnostic tests, including those used for measuring copy number alterations.

In some embodiments, a reference sequence that is present at two copies per diploid genome can be used, e.g., a housekeeping gene (e.g., a gene that is required for the maintenance of basic cellular function). Dividing the concentration or amount of the target by the concentration or amount of the reference can yield an estimate of the number of target copies per genome.

A housekeeping gene that can be used as reference in the methods described herein can include a gene that encodes a transcription factor, a transcription repressor, an RNA splicing gene, a translation factor, tRNA synthetase, RNA binding protein, ribosomal protein, RNA polymerase, protein processing protein, heat shock protein, histone, cell cycle regulator, apoptosis regulator, oncogene, DNA repair/replication gene, carbohydrate metabolism regulator, citric acid cycle regulator, lipid metabolism regulator, amino acid metabolism regulator, nucleotide synthesis regulator, NADH dehydrogenase, cytochrome C oxidase, ATPase, mitochondrial protein, lysosomal protein, proteosomal protein, ribonuclease, oxidase/reductase, cytoskeletal protein, cell adhesion protein, channel or transporter, receptor, kinase, growth factor, tissue necrosis factor, etc. Specific examples of housekeeping genes that can be used in the methods described include, e.g., HSP90, Beta-actin, tRNA, rRNA, ATF4, RPP30, and RPL3.

A single copy reference nucleic acid (e.g., gene) can be used to determine copy number variation. Multi-copy reference nucleic acids (e.g., genes) can be used to determine copy number to expand the dynamic range. For example, the multi-copy reference gene can comprise about, or more than about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1000, 2000, 3000, 4000, 5000, 6000, 7000, 8000, 9000, 10,000, 20,000, 30,000, 40,000, 50,000, 60,000, 70,000, 80,000, 90,000, or 100,000 copies in a genome.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

EXAMPLES

Example 1

One thousand genome equivalents (about 6 ng of DNA) can be sequenced at 100× depth. From 1000 genome equivalents, there can be 2,000 copies of every (normal copy number) target. Steps can be taken such that for every locus, a large majority of fragments end up in separate partitions. Steps can also be taken to ensure that most of the 2,000 fragments are tagged with a unique barcode.

The first goal can be accomplished by increasing the number of partitions. For example, with 100,000 partitions, only about 0.5% of fragments at a particular locus from different chromosomes are expected to end up in the same partition. Note that many such cases will be readily identified by the appearance of distinct alleles from heterozygous SNPs with the same barcode as well as by increased coverage of the locus by a barcode.

In order to ensure that most fragments are tagged with distinct barcodes, a large number of different barcodes can be used, and an approach that distributes barcodes so that any given partition is furnished with a small number (preferably one) of barcode-containing droplets can be used. The distribution can be random so that some partitions receive zero barcodes, some one, some multiple. Thus, for 100,000 partitions 100,000 barcoding droplets can be supplied. In this case, it is anticipated that 37% of the partitions will receive no adaptors and will thus be unavailable for sequencing. The number of barcoding droplets can be increased if sample preservation is a goal. 37% of the partitions can be barcoded with a single barcode and up to 25% can be coded with potentially different barcodes. In the case above, 740 fragments will be unavailable for sequencing, 740 will be sequestered in with their own barcodes and 500 will be sequestered with multiple barcodes. Ideally all of the 740*1+360*2+ . . . =2,000 barcodes in the partitions associated with a particular fragment would be unique. If there are 10,000 different barcode types, then more than 80% of the fragments would be uniquely tagged.

If the number of genome equivalents is lower then fewer partitions and barcodes could be used.

Note that perfection is not necessary for this application, because only a small subset of SNPs from any given genomic location can be captured to yield phasing information. It can be acceptable if a substantial fraction of fragments is not informative.

One can attain greater efficiency of sample processing if each partition is supplied with a barcode in a controlled manner. For example, sample containing partitions and barcode containing partitions can be merged using droplet merging technology from RAINDANCE™ (RAINSTORM™). Droplet merging can be performed using a microfluidic circuit similar to FLUIDIGM's array designs. If it can be guaranteed that a given partition receives precisely one ADF, fewer ADFs and fewer ADF types can be used.

A microfluidic chip can be used in an analogous manner for partitioning. Sample partitions can be supplied with their own barcodes via a two-dimensional arrangement of channels as described above. A large number of unique barcodes can be readily supplied by combining vertical and horizontal barcodes.

While preferred embodiments of the methods, compositions, systems, and kits described herein have been shown and described herein, it will be obvious to those skilled in the art that such embodiments are provided by way of example only. Numerous variations, changes, and substitutions will now occur to those skilled in the art without departing from the methods, compositions, systems, and kits described herein. It should be understood that various alternatives to the embodiments of the methods, compositions, systems, and kits described herein may be employed in practicing the methods, compositions, systems, and kits. It is intended that the following claims define the scope of the methods, compositions, systems, and kits within the scope of these claims and their equivalents be covered thereby.

What is claimed is:

1. A composition comprising a plurality of second partitions containing first partitions, wherein:
   a. said first partitions are degradable upon the application of a stimulus to said first partitions such that contents of a first partition is mixed with contents of a second partition; and
   b. said first partitions are contained within the second partitions;
   c. said first partitions contain an oligonucleotide barcode; and
   d. the first partitions have on average a first average volume and the second partitions have on average a second average volume, wherein the second average volume is at least twice as large as the first average volume.

2. The composition of claim 1, wherein said stimulus is selected from the group consisting of a biological, chemical, thermal, electrical, magnetic, or photo stimulus, and combination thereof.

3. The composition of claim 1, wherein said stimulus is a chemical stimulus.

4. The composition of claim 1, wherein said second partition is a droplet.

5. The composition of claim 1, wherein the first partition is a droplet.

6. The composition of claim 1, wherein the first partition and the second partition are droplets.

7. The composition of claim 1, wherein the second partition comprises a sample comprising polynucleotides.

8. The composition of claim 7, wherein the second partition further comprises a DNA polymerase enzyme or a reverse transcriptase enzyme.

9. The composition of claim 7, wherein the polynucleotides comprise DNA.

10. The composition of claim 9, wherein the DNA is genomic DNA.

11. The composition of claim 7, wherein the polynucleotides comprise RNA.

12. The composition of claim 7, wherein the polynucleotides comprise cDNA.

13. The composition of claim 7, wherein the partitions are less than 10 nL in volume.

14. A device comprising a plurality of second partitions, wherein:
   a. at least one second partition of the plurality of second partitions contains a first partition comprising an oligonucleotide barcode, and the first partition has a first volume and the at least one second partition has a second volume, wherein the second volume is at least twice as large as the first volume; and
   b. said first partition is degradable upon the application of a stimulus to said first partition such that contents of a first partition is mixed with contents of a second partition.

15. The device of claim 14, wherein said second partition is a droplet.

16. The device of claim 14, wherein said stimulus is selected from the group consisting of a biological, chemical, thermal, electrical, magnetic, or photo stimulus, and a combination thereof.

17. The device of claim 16, wherein said stimulus is a chemical stimulus.

18. The device of claim 14, wherein the first partition is a droplet.

19. The device of claim 14, wherein the first partition and the second partition are droplets.

20. The device of claim 19, wherein the droplets are less than 10 nL in volume.

21. The device of claim 14, wherein the second partition comprises a sample comprising polynucleotides.

22. The device of claim 21, wherein the second partition further comprises a DNA polymerase enzyme or a reverse transcriptase enzyme.

23. The device of claim 21, wherein the polynucleotides comprise DNA.

24. The device of claim 23, wherein the DNA is genomic DNA.

25. The device of claim 21, wherein the polynucleotides comprise RNA.

26. The device of claim 21, wherein the polynucleotides comprise cDNA.

* * * * *